US006248716B1

(12) United States Patent
Deigin et al.

(10) Patent No.: US 6,248,716 B1
(45) Date of Patent: Jun. 19, 2001

(54) PEPTIDE, A METHOD FOR ITS PREPARATION AND A PHARMACEUTICAL COMPOSITION CONTAINING THE PEPTIDE

(75) Inventors: Vladislav I. Deigin, North York (CA); Elena P. Yarova, Moscow (RU)

(73) Assignee: Immunotech Developments Inc., North York (CA)

( * ) Notice: Subject to any disclaimer, the term of this patent is extended or adjusted under 35 U.S.C. 154(b) by 0 days.

(21) Appl. No.: 09/320,667

(22) Filed: May 27, 1999

Related U.S. Application Data

(63) Continuation-in-part of application No. 08/681,248, filed on Jul. 22, 1996, now Pat. No. 6,184,208, which is a continuation-in-part of application No. 08/594,995, filed on Jan. 31, 1996, now abandoned, which is a continuation-in-part of application No. PCT/RU95/00138, filed on Jun. 27, 1995.

(51) Int. Cl.[7] ..................................................... A61K 38/00
(52) U.S. Cl. ................................ 514/17; 514/18; 530/330
(58) Field of Search ........................ 514/17, 18; 530/330

(56) References Cited

FOREIGN PATENT DOCUMENTS

194961 * 9/1983 (NZ).
9421242 * 9/1994 (WO).

OTHER PUBLICATIONS

Degrado, Advances in Protein Chemistry, vol. 39, pp. 51–124, 1988.*
CAPLUS, DN 128:12263, Lishmanov et al., Bull, Exp. Biol. Med., 123(3), (1997), 239–241 (abstract).*
CAPLUS, DN 109:183821, Inoue et al., Kyorin Igakkai Zasshi, 19(2), (1988), 151–8 (abstract).*
CAPLUS, DN 101:129076, Panksepp et al., Peptides, 5(4), (1984), 829–31 (abstract).*
CAPLUS, DN 109:231554, Blondell, JP 63044595, Feb. 25, 1988 (abstract).*
CAPLUS, DN 107:191140, Sato et al., J. Pharmacol. Exp. Thr., 242(2), (1987), 654–9 (abstract).*
CAPLUS, DN 104:82650, Suzuki et al., Chem. Pharm. Bull., 33(11), (1985), 4865–9 (abstract).*
CAPLUS, DN 124:279588, Fleishman et al., Byull. Exp. Biol. Med., 118(11), 1994, 508–10 (abstract).*

* cited by examiner

Primary Examiner—Dwayne C. Jones
Assistant Examiner—C. Delacroix-Muirheid
(74) Attorney, Agent, or Firm—Micheline Gravelle; Bereskin & Parr

(57) ABSTRACT

A peptide of the formula I $$\text{X-Tyr-Y-Phe-Z-A} \qquad \text{I}$$

wherein X is hydrogen, arginine, D-arginine, ornithine, D-ornithine, lysine, D-lysine, homoarginine, D-homoarginine, citrulline, D-citrulline; Tyr is tyrosine; Y is D-alanine, D-valine, D-leucine, D-isoleucine, D-phenylalanine, D-asparagine, D-tryptophan, D-proline, D-serine, D-threonine, D-tyrosine, D-hydroxyproline, D-cysteine, D-cysteyl-cysteine, D-methionine, D-lysine, D-homoarginine, D-arginine, D-histidine, D-aspartic acid, D-glutamic acid, D-β-alanine, or D-ornithine; Phe is phenylalanine; Z is alanine, D-alanine, valine, D-valine, leucine, D-leucine, isoleucine, D-isoleucine, phenylalanine, D-phenylalanine, asparagine, D-asparagine, glycine, glutamine, D-glutamine, tryptophan, D-tryptophan, proline, D-proline, serine, D-serine, threonine, D-threonine, tyrosine, D-tyrosine, hydroxyproline, D-hydroxyproline, cysteine, D-cysteine, cysteyl-cysteine, cysteine-D-cysteine, D-cysteyl-cysteine, D-cysteine-D-cysteine, methionine, D-methionine, lysine, D-lysine, arginine, D-arginine, histidine, D-histidine, aspartic acid, D-aspartic acid, glutamic acid, D-glutamic acid, β-alanine, D-β-alanine, ornithine, or D-ornithine; and A is hydroxyl or substituted amide ($C_1$–$C_3$); compositions containing same and its use in modulating physiological processes such as weight gain, activities of the epithelium growth zone, hair growth, wound healing, and to stimulate reparative and anabolic processes, exert analgesic effects and to reduce stress.

13 Claims, 6 Drawing Sheets

PEPTIDE, A METHOD FOR ITS PREPARATION AND A PHARMACEUTICAL COMPOSITION CONTAINING THE PEPTIDE

This application is a continuation-in-part of U.S. patent application Ser. No. 08/681,248 filed Jul. 22, 1996 now U.S. Pat. No. 6,184,208 which is a continuation-in-part of U.S. patent application Ser. No. 08/594,995, filed Jan. 31, 1996, now abandoned, which is a continuation-in-part of PCT/RU95/00138 filed Jun. 27, 1995 designating the United States.

FIELD OF THE INVENTION

The invention relates to a biologically active peptide; a novel pharmaceutical composition containing the peptide; a method for preparing the peptide; and uses of the peptide.

BACKGROUND OF THE INVENTION

Hormones are known to control the metabolic processes both in growing and mature organisms. Peptides often act as hormones. They are not only hormonally active themselves but regulate the action of other hormones, which control the vital activity of the organism. However, the potential of such natural compounds is limited. Therefore, many scientific laboratories have tried to develop methods for preparing synthetic derivatives of natural peptides, which are more active than their natural analogues (EP 0136720, 1984; EP 0137904, 1984). Moreover, new peptides have been synthesized, which are absent in the organism but have unique properties. Among them there is a special group of physiologically active peptides directly or indirectly controlling the action of hormones such as the growth hormone. Some of these active peptides increase the growth hormone level in blood (PCT 89/07111, 1989; PCT 91/16923, 1991) while others suppress the hormone (FR 2235701, 1978; FR 2532308, 1982).

A peptide which activates the growth of the epidermal layer in man (PCT 90/13570, 1990), and a metal-containing peptide, which has a significant stimulating effect on hair growth in warm-blooded animals (PCT 91/07431, 1991) have been synthesized. Another peptide analogue has been reported to facilitate hair removal in animals (FR 2487677, 1982).

Different peptide compositions evidently make it possible to control metabolic processes. The most promising task is, however, the development of compounds and preparations with many-sided actions.

At present, there are only a few peptides with comprehensive actions, for instance, the analogue of the P substance described in U.S. Pat. No. 4,680,283. The peptide synthesized as described in the patent has a range of useful properties. Its acts as a biostimulator, and has an analgesic effect similar to that of morphine.

Many studies have shown the importance of synthesizing peptides with opiate-like properties. Unfortunately, the production of morphine-like compounds from natural sources is limited by the complexity of the manufacturing processes (U.S. Pat. No. 4,042,682, 1977). This circumstance resulted in the creation of an arsenal of synthetic analogues (U.S. Pat. No. 4,681,871, 1987; EP 0112036, 1983; EP 0221019, 1986).

Some opiate-like peptides have become known and clinically used in the treatment of brain ischemia (DE 3447720, 1985; U.S. Pat. No. 4,684,624, 1987), for pain relief in pregnant women (EP 0099173, 1984), and only as analgesics. They are reported to be especially effective when used in combination with conventional drug therapy in many diseases (EP 096592, 1983; EP 0099286, 1984; U.S. Pat. No. 4,123,523, 1987).

However, the known synthetic peptides cannot completely satisfy all medical requirements, since they do not have the necessary combination of properties, which would increase their effectiveness. Furthermore, many of them are effective only in large doses that can cause side effects.

Certain peptide formulations, such as a D-phenylalanine-containing preparation, have an anti-stress effect (Economic patent GDR N 229931, A 61 K 31/195).

There is also a recognized method for obtaining anti-stress drugs, which are long-chain semisynthetic products with the last 5–12 amino acids identified (Economic patent GDR N 229593, A 61 K 37/02). These drugs are obtained in a rather complicated way, the structure of their active elements is not quite clear.

Dibazol can be used as an anti-stress drug (Mashkovsky M. D. Drugs, Kharkov, Torsing, 1998, ed. 13, v.1, p.432). The drawback of Dibazol, however, is its spasmolytic effect that may restrict the drug use as stress-corrector.

SUMMARY OF THE INVENTION

The present inventors have prepared peptides which have a wide range of biological activities. In particular, the peptides have been found to influence physiological processes such as weight gain, activities of the epithelium growth zone including hair growth, wound healing, and to stimulate reparative and anabolic processes, and exert analgesic effects. The peptides are also useful in reducing stress caused by, for example, physical, mental or chemical factors of the environment.

Broadly stated the present invention relates to a peptide of the formula I

    I wherein X is hydrogen, arginine, D-arginine, ornithine, D-ornithine, lysine, D-lysine, homoarginine, D-homoarginine, citrulline, D-citrulline; Tyr is tyrosine; Y is D-alanine, D-valine, D-leucine, D-isoleucine, D-phenylalanine, D-asparagine, D-tryptophan, D-proline, D-serine, D-threonine, D-tyrosine, D-hydroxyproline, D-cysteine, D-cysteyl-cysteine, D-methionine, D-lysine, D-homoarginine, D-arginine, D-histidine, D-aspartic acid, D-glutamic acid, D-β-alanine, or D-ornithine; Phe is phenylalanine; Z is alanine, D-alanine, valine, D-valine, leucine, D-leucine, isoleucine, D-isoleucine, phenylalanine, D-phenylalanine, asparagine, D-asparagine, glycine, glutamine, D-glutamine, tryptophan, D-tryptophan, proline, D-proline, serine, D-serine, threonine, D-threonine, tyrosine, D-tyrosine, hydroxyproline, D-hydroxyproline, cysteine, D-cysteine, cysteyl-cysteine, -cysteine-D-cysteine, D-cysteine-cysteine, D-cysteine-D-cysteine, methionine, D-methionine, lysine, D-lysine, arginine, D-arginine, histidine, D-histidine, aspartic acid, D-aspartic acid, glutamic acid, D-glutamic acid, β-alanine, D-β-alanine, ornithine, or D-ornithine; and A is hydroxyl or an amide which may be substituted.

The invention also relates to analogs and derivatives of the peptides.

The invention also relates to a pharmaceutical composition comprising one or more peptides of the invention and a pharmaceutically acceptable carrier.

The invention also includes a method of modulating physiological processes in a subject such as weight gain, activities of the epithelium growth zone including hair growth, and wound healing comprising administering an effective amount of a peptide of the present invention to an animal in need thereof.

The invention also relates to a method of stimulating reparative and anabolic processes, and exerting analgesic effects comprising administering an effective amount of a peptide of the present invention to an animal in need thereof.

The invention further relates to a method of reducing or preventing stress comprising administering an effective amount of a peptide of the present invention to an animal in need thereof.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE FIGURES

The present invention will be more fully understood when the detailed description is read together with the following Figures in which.

Figure 1:
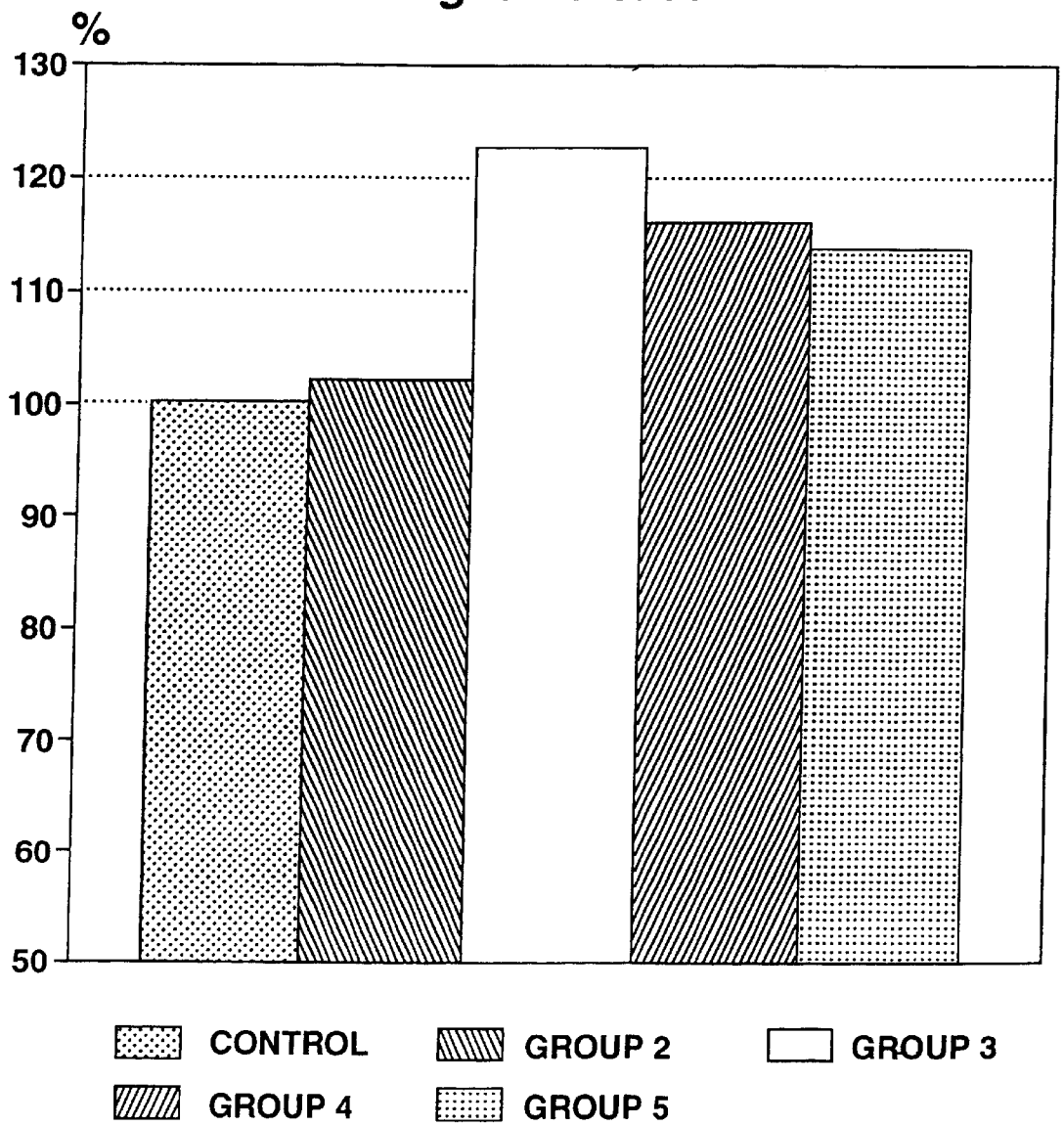
FIG. 1 is a graph showing the weight gain of cockerels administered a peptide in accordance with the present invention compared with a control group.

DETAILED DESCRIPTION OF THE INVENTION (1) Peptides of the Invention

As mentioned previously, the present invention relates to a peptide of the formula I

wherein X is hydrogen, arginine, D-arginine, ornithine, D-ornithine, lysine, D-lysine, homoarginine, D-homoarginine, citrulline, D-citrulline; Tyr is tyrosine; Y is D-alanine, D-valine, D-leucine, D-isoleucine, D-phenylalanine, D-asparagine, D-tryptophan, D-proline, D-serine, D-threonine, D-tyrosine, D-hydroxyproline, D-cysteine, D-cysteyl-cysteine, D-methionine, D-lysine, D-homoarginine, D-arginine, D-histidine, D-aspartic acid, D-glutamic acid, D-β-alanine, or D-ornithine; Phe is phenylalanine; Z is alanine, D-alanine, valine, D-valine, leucine, D-leucine, isoleucine, D-isoleucine, phenylalanine, D-phenylalanine, asparagine, D-asparagine, glycine, glutamine, D-glutamine, tryptophan, D-tryptophan, proline, D-proline, serine, D-serine, threonine, D-threonine, tyrosine, D-tyrosine, hydroxyproline, D-hydroxyproline, cysteine, D-cysteine, cysteyl-cysteine, cysteine-D-cysteine, D-cysteyl-cysteine, D-cysteine-D-cysteine, methionine, D-methionine, lysine, D-lysine, arginine, D-arginine, histidine, D-histidine, aspartic acid, D-aspartic acid, glutamic acid, D-glutamic acid, β-alanine, D-β-alanine, ornithine, or D-ornithine; and, A is hydroxyl or an amide which may be substituted.

In a preferred embodiment of the invention, a peptide of the formula I as defined above is provided, wherein when X is Arg and Y is D-Ala, the Z is not Pro. In another embodiment of the invention, when X is D-Arg and Y is D-Arg then Z is not D-Ala. In a further preferred embodiment of the peptide, when X is H and Y is D-Arg, Z-A is not Lys-NH$_2$; and when X is H, and Y is Pro, Z-A is not Pro-OH or Pro-NH$_2$.

In an embodiment of the invention a peptide of the formula I is provided, wherein X is Arg, D-Arg, D-Orn, homoarginine, D-homoarginine, or citrulline, Y is D-orn, D-ala, or D-Arg; Z is D-Ala, Gly, Pro, D-Pro or β-Ala; and A is OH or NH$_2$. Preferred peptides of the present invention comprise peptides of the formula I wherein X is Arg, homoarginine, D-homoarginine, citrulline, or D-citrulline; Y is D-Ala, D-Orn, or D-Arg; Z is D-Ala; and A is OH or NH$_2$. In another preferred embodiment, X is Arg; Y is D-Ala; Z is D-Pro, Pro, or β-Ala; and, A is OH.

Preferred peptides of the present invention include H-D-Arg-Tyr-D-Arg-Phe-D-Ala-NH$_2$, H-D-Orn-Tyr-D-Ala-Phe-D-Ala-OH, H-Arg-Tyr-D-Ala-Phe-β-Ala-OH, H-Arg-Tyr-D-Ala-Phe-Gly-OH; H-Har-Tyr-D-Arg-Phe-D-Ala-NH$_2$; H-D-Har-Tyr-D-Arg-Phe-D-Ala-NH$_2$; H-Cyt-Tyr-D-Arg-Phe-D-Ala-NH$_2$; H-D-Cyt-Tyr-D-Arg-Phe-D-Ala-NH$_2$; H-Arg-Tyr-D-Ala-Phe-Pro-OH; H-Arg-Tyr-D-Ala-Phe-D-Pro-OH; H-Arg-Tyr-D-Ala-Phe-β-Ala-OH; H-Arg-Tyr-D-Orn-Phe-D-Ala-OH; H-Arg-Tyr-D-Arg-Phe-D-Ala-OH; H-Arg-Tyr-D-Arg-Phe-β-Ala-NH$_2$; H-Tyr-D-Orn-Phe-D-Glu-OH. A most preferred peptide of the invention is: H-Arg-Tyr-D-Ala-Phe-Gly-OH.

The following standard abbreviations for the amino acid residues are used throughout the specification: Ala-alanine; Cys-cysteine; Asp-aspartic acid; Glu-glutamic acid; Phe-phenylalanine; Gly-glycine; His-histidine; Ile-isoleucine; Lys-lysine; Leu-leucine; Met-methionine; Asn-asparagine; Pro-proline; Gln-glutamine; Arg-arginine; Ser-serine; Thr-threonine; Val-valine; Trp-tryptophan; Tyr-tyrosine; Orn-ornithine; Har-homoarginine; Cyt-citrulline; Hyp-hydroxyproline; and Cys-Cys-cysteyl-cysteine.

The peptides included in the present invention includes all peptides of the formula I (as defined above) as well as all analogs, derivatives and salts of the peptides of the formula I.

Analogs of the peptide of the Formula I may include, but are not limited to, the peptide of the Formula I containing one or more amino acid insertions or deletions. Amino acid insertions may consist of a single amino acid residue or sequential amino acids. The term "analog" also includes any peptide having an amino acid residue sequence substantially identical to a peptide sequence specifically shown herein in which one or more residues have been conservatively substituted with a functionally similar residue and which displays the ability to mimic the peptides as described herein. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue in place of a non-derivatized residue provided that such polypeptide displays the requisite activity.

Analogs of the peptide of the invention exhibit the activity characteristic of the peptide and may further possess additional advantageous features such as increased bioavailability, stability, or reduced host immune recognition.

The term "derivative" refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The invention further includes cyclic derivatives of the peptides of the invention. Cyclization allows the peptide to assume a more favourable conformation. Cyclization of the peptides may be achieved using techniques known in the art. In particular, disulfide bonds may be formed between two appropriately spaced components having free sulfhydryl groups. The bonds may be formed between side chains of amino acids, non-amino acid components, or a combination of the two.

Peptides of the invention may be converted into pharmaceutical salts by reacting with inorganic acids including hydrochloric acid, sulfuric acid, hydrobromic acid, phosphoric acid, etc., or organic acids including formic acid, acetic acid, propionic acid, glycolic acid, lactic acid, pyruvic acid, oxalic acid, succinic acid, malic acid, tartaric acid, citric acid, benzoic acid, salicylic acid, benezenesulfonic acid, and toluenesulfonic acids.

The peptides of the invention may be prepared using recombinant techniques. Nucleic acid molecules which encode a peptide of the invention may be incorporated in a known manner into an expression vector which ensures good expression of the peptide. Suitable expression vectors include but are not limited to cosmids, plasmids, or modified viruses so long as the vector is compatible with the host cell used. The expression vectors contain a nucleic acid molecule encoding a peptide of the invention and regulatory sequences necessary for the transcription and translation of the inserted protein-sequence. Regulatory sequences may be obtained from a variety of sources, such as bacterial, fungal, viral, mammalian, or insect genes [See the regulatory sequences described in Goeddel, Gene Expression Technology: Methods in Enzymology 185, Academic Press, San Diego, Calif. (1990)]. The selection of regulatory sequences is dependent on the host cell chosen, and may be readily accomplished by one of ordinary skill in the art. Sequences, including an origin of replication, additional DNA restriction sites, enhancers, and sequences conferring inducibility of transcription may also be incorporated into the expression vector.

A selectable marker gene which facilitates the selection of transformed or transfected host cells may also be included in the recombinant expression vector. Examples of selectable marker genes are genes encoding proteins such as G418 and hygromycin which confer resistance to certain drugs, β-galactosidase, chloramphenicol acetyltransferase, and firefly luciferase. It will be appreciated that the selectable markers may be introduced on a separate vector from the nucleic acid. The invention also includes a peptide of the invention conjugated with a selected protein, or a selectable marker (see below) to produce fusion proteins.

Genes may also be included in the recombinant expression vectors which encode a fusion portion which provides increased expression of the recombinant peptide; increased solubility of the recombinant peptide; and/or aid in the purification of the recombinant peptide by acting as a ligand in affinity purification. In particular, a proteolytic cleavage site may be inserted to allow separation of the recombinant peptide from the fusion portion after purification of the fusion protein.

A recombinant expression vector may be introduced into a host cell to produce a transformant host cell. Transformant host cells include prokaryotic and eukaryotic cells transformed or transfected with a recombinant expression vector of the invention. The terms "transformed with", "transfected with", "transformation" and "transfection" include the introduction of nucleic acid (e.g. a vector) into a host cell by one of many techniques known in the art. Examples of methods for transforming and transfecting host cells may be found in Sambrook et al. (Molecular Cloning: A Laboratory Manual, 2nd Edition, Cold Spring Harbor Laboratory press (1989)), and other laboratory textbooks.

Suitable host cells include prokaryotic and eukaryotic host cells. In particular, the peptides of the invention may be expressed in bacterial cells such as E. coli, insect cells (using baculovirus), yeast cells or mammalian cells. Other suitable host cells are described in Goeddel, Gene Expression Technology: Methods in Enzymology 185, Academic Press, San Diego, Calif. (1991).

In the alternative, the peptides of the invention may be prepared by chemical synthesis using techniques known in the chemistry of proteins such as solid phase synthesis (Merrifield, 1964, J. Am. Chem. Assoc. 85:2149–2154) or synthesis in homogenous solution (Houbenweyl, 1987, Methods of Organic Chemistry, ed. E. Waünsch, Vol. 15 I and II, Thieme, Stuttgart).

According to an embodiment of the present invention, the peptide of the formula (I) is synthesized by step-by-step building of the peptide chain beginning with the C-terminal amino acid Z in the form of a substituted amide or an amino acid with a protected carboxyl group. N-protected phenylalanine is then attached using the method of activated esters or mixed anhydrides and the N-protecting group is removed. The next amino acid is attached using the method of activated esters or mixed anhydrides, and the N-protected group is then removed. The following N-protected amino acid is then added using the same procedure. When the chain building is completed, the tetra- or penta-peptide is deblocked, the peptide is obtained by hydrogenolysis in the presence of a palladium catalyst, and the final product is isolated. The peptide prepared using this process is a white powder with a yellowish or greyish tinge, soluble in water, substantially insoluble in alcohol, and substantially insoluble in chloroform.

N-terminal or C-terminal fusion proteins comprising a peptide of the invention conjugated with other molecules such as proteins or selectable markers may be prepared by fusing, through recombinant techniques, the N-terminal or C-terminal of the peptide, and the sequence of a selected protein or selectable marker with a desired biological function. The resulting fusion proteins contain the peptide fused to the selected protein or marker protein as described herein. Fusion proteins may also be prepared using the step-by-step synthesis described herein.

Monoclonal or polyclonal antibodies specific for the peptides of the invention may be prepared using conventional methods. For example, the preparation of monoclonal antibodies can be carried out as described in Goding, J. W., Monoclonal Antibodies: Principles and Practice, 2nd Ed., Academic Press, London, 1986.

The peptides of the invention may be labelled using conventional methods with various enzymes, fluorescent materials, luminescent materials and radioactive materials. Suitable enzymes, fluorescent materials, luminescent materials, and radioactive material are well known to a person skilled in the art.

(2) Pharmaceutical Compositions and uses of the Peptide

The peptides of the present invention can be formulated into pharmaceutical compositions and used for many purposes. The peptides have significant opiate-like effects and accordingly may be used as an analgesic, hypnotic, and diaphoric, and in spasmodic conditions. The peptides also exhibit an anabolic effect an can be used to increase body weight, stimulate the activity of the growth zone and growth of the epidermal layer, including hair. The biostimulating properties of the claimed peptide are manifested in wound healing and reparative processes. The peptides can also be used to reduce or prevent stress.

"Stress" as used herein pertaines to any factor which may potentially result in a physiological change in an organism. "Physiological" as used herein pertains to any function or activity of an organism or one or any of its parts. Accordingly, the present invention includes a method of modulating physiological processes in a subject such as weight gain, activities of the epithelium growth zone including hair growth, and wound healing comprising administering an effective amount of a peptide of the present invention to an animal in need thereof.

The invention also relates to a method of stimulating reparative and anabolic processes, and exerting analgesic effects comprising administering an effective amount of a peptide of the present invention to an animal in need thereof.

The invention further relates to a method of reducing or preventing stress comprising administering an effective amount of a peptide of the present invention to an animal in need thereof.

The term "effective amount" as used herein is an amount effective, at dosages and for periods of time necessary to achieve the desired result. An effective amount of a peptide may vary according to factors such as the disease state, age, sex, and weight of the individual. Dosage regime may be altered to provide the optimum therapeutic response.

The term "animal" as used herein includes all members of the animal kingdom including humans, cockerels, mink, arctic fox, domestic animals such as pigs, cows, goats, and bulls.

The pharmaceutical compositions of the invention can be prepared by per se known methods for the preparation of pharmaceutically acceptable compositions which can be administered to subjects, such that an effective quantity of a peptide is combined in a mixture with a pharmaceutically acceptable vehicle. Examples of pharmaceutically acceptable vehicles are described in Remington's Pharmaceutical Sciences (Remington's Pharmaceutical Sciences, Mack Publishing Company, Easton, Pa., USA 1985).

The peptides may be administered by injection (subcutaneous, intravenous, etc.), oral administration, inhalation, transdermal application, or rectal administration. Depending on the route of administration, the peptides in the pharmaceutical compositions may be coated in a material to protect them from the action of enzymes. Organic substances may also be included in the compositions to prolong the pharmacologic actions of the peptides. Examples of such organic substances include non-antigenic gelatin, carboxymethylcellulose, sulfonate or phosphate ester of alginic acid, dextran, polyethylene glycol and other glycols, phytic acid, polyglutamic acid, and protamine.

Compositions for injection include, albeit not exclusively, the peptides in association with one or more pharmaceutically acceptable vehicles or diluents, and contained in buffered solutions With a suitable pH and iso-osmotic with the physiological fluids. Any pharmaceutically suitable diluent can be used in the composition for injections: distilled water, physiological or a salt solution, and/or a buffer solution. The composition for injections may be prepared by conventional volume-weight procedure. A certain amount of the peptide is diluted to the necessary volume with a diluent or solvent. Then the solution is filtered through sterilized filters, bottled or ampouled. The resultant solution is a stable transparent liquid, and does not contain any chemical or other impurities.

In a preferred embodiment of the invention, the composition generally contains 0.001 or 0.1% (preferably 0.001–0.01%) of the peptide. The percentage also depends on the medicinal form—solution or a solid form. The preferred pharmaceutical composition is made by mixing the carrier and the peptide at a temperature of 40–70° C. The composition is stable in solution for at least 24 hours at a temperature of 70° C. (20° C.).

In one embodiment, the peptide is dissolved in dimethylsulfoxide and polyethylene oxide-400, preferably in a weight ratio of peptide:dimethylsulfoxide:polyethyle oxide of about 1:1:98. In another embodiment, the peptide is dissolved in dimethyl sulfoxide and olive oil, preferably in a weight ratio of peptide:dimethyl sulfoxide:olive oil of about 1:10:89. Such compositions provide the peptide in a prolonged release formulation suitable for parenteral administration.

Solid form preparations for oral administration can be made in the form of tablets, powders, capsules. It may contain a medium for the active substance and other additives, including dyes, aromas, etc. The peptide percentage may be from 0.001% to 0.1% and usually depends on the type of the composition for oral use.

The utility of the peptides and pharmaceutical compositions of the invention may be confirmed in in vivo animal experimental model systems.

The following non-limiting examples are illustrative of the present invention.

EXAMPLE 1
Preparation of H-Arg-Tyr-D-Ala-Phe-Gly-OH (a) Preparation of Butoxycarbonyl (Boc)-Phe-Gly-oBzl A mixture of 10.7 g (40.0 mmol) Boc-Phe-OH and 4.8 ml (40.1 mmol) N-methyl morpholine in 50 ml dimethylformamide (DMF) was cooled to −15° C. Then 5.6 g (40.0 mmol) isobutyl chloroformate was added with mixing. Two minutes later, a cooled solution of 13.1 g (40.0 mmol) glycine benzyl ester p-toluenesulfonate in 50 ml DMF was added to the solution. The reaction mixture was stirred at −15° C. for 30 minutes, and then for 2 hours at ambient temperature. DMF was removed by evaporation under vacuum, and the residue was combined with 100 ml ethyl acetate, rinsed twice with 50 ml of 2% sulfuric acid solution, rinsed twice with 80 ml saturated sodium bicarbonate solution, then rinsed with water to neutral pH, and dried over anhydrous sodium sulfate. The ethyl acetate layer was evaporated under vacuum. The residue was crystallized from ethyl acetate with the addition of ether and hexane. The yield was 16.4 g (98.2%). Melting point was 135.2° C. $R_f$=0.71 in chloroform:ethyl acetate:methanol=3:6:1. $R_f$=0.62 in ethyl acetate:hexane=1:1.

(b) Preparation of Boc-D-Ala-Phe-Gly-oBzl 16.4 g (39.8 mmol) Boc-Phe-Gly-oBzl was dissolved in 80 ml of 50% trifluoroacetic acid (TFA) in chloroform. After 1 hour the solvents were removed by evaporation under vacuum, leaving a thick oil. The residue was flooded with 150 ml diethyl ether and crystallized. The precipitate was filtered, washed with ether, and air dried. The yield was 16.2 g (99.8%). Melting point of TFA•H-Phe-Gly-oBzl was 135° C. $R_f$=0.34 in chloroform:methanol=9:1.

A mixture of 7.5 g (39.7 mmol) Boc-D-Ala-OH and 4.6 ml (40.0 mmol) N-methyl morpholine in 50 ml DMF was cooled to −15° C. and 5.6 g (40.3 mmol) isobutyl chloroformate was added during mixing. Two minutes later, a cooled solution of 16.2 g (40.0 mmol) H-Phe-Gly-oBzl trifluoracetate and 4.6 ml (40.0 mmol) N-methyl morpholine in 50 ml DMF was added. The reaction mixture was stirred at −15° C. for 30 minutes, and then for 2 hours at ambient temperature. DMF was removed by evaporation under vacuum. The residue was combined with 100 ml ethyl acetate, and rinsed twice with 50 ml of 2% sulfuric acid solution, rinsed twice with 80 ml saturated sodium bicarbonate solution, rinsed with water to neutral pH, and dried over anhydrous sodium sulfate. The ethyl acetate layer was evaporated under vacuum. The residue was crystallized from ether. The yield was 14.5 g (75.9%). Melting point was 140° C. $R_f$=0.79 in chloroform:ethyl acetate:methanol=6:3:1. $R_f$=0.55 in chloroform:methanol=9:1.

(c) Preparation of Boc-Tyr(Boc)-D-Ala-Phe-Gly-oBzl 14.4 g (29.8 mmol) Boc-D-Ala-Phe-Gly-oBzl was dissolved in 80 ml of 50% TFA in chloroform. After one hour, the solvents were removed by evaporation under vacuum leaving a thick oil. The residue was dissolved in 50 ml DMF, and to this was added 3.4 ml (29.8 mmol) N-methyl morpholine. A mixture of 11.4 g (30.0 mmol) Boc-Tyr(Boc)-OH and 3.45 ml (30.0 mmol) N-methyl morpholine in 50 ml DMF was cooled to −15° C. and to this was added 4.27 g (30.0 mmol) isobutyl chloroformate with mixing. Two minutes later, a cooled solution of 14.3 g (29.8 mmol) benzyl ester of the tripeptide H-D-Ala-Phe-Gly-oBzl was added. The reaction mixture was stirred at −15° C. for 30 minutes, and then for 2 hours at ambient temperature. DMF was removed by evaporation under vacuum. The residue was combined with 100 ml of ethyl acetate, rinsed twice with 50 ml of 2% sulfuric acid solution, rinsed twice with 80 ml of saturated sodium bicarbonate solution, rinsed with water to neutral pH, and dried over anhydrous sodium sulfate. The ethyl acetate layer was evaporated under vacuum. The residue was crystallized from ethyl acetate. The yield was 8.5 g (83.4%). Melting point was 133.5° C. $R_f$=0.62 in chloroform:ethyl acetate:methanol=6:3:1. $R_f$=0.57 in chloroform:methanol=9:1.

(d) Preparation of Boc-Arg (NO$_2$)-Tyr-D-Ala-Phe-Gly-oBzl 9.8 g (13.1 mmol) Boc-Tyr(Boc)-D-Ala-Phe-Gly-oBzl was dissolved in 80 ml of 50% TFA in chloroform. After 1 hour the solvents were removed by evaporation under vacuum leaving a thick oil. The residue was crystallized from ether. The yield was 9.68 g (100%).

9.6 g (13.0 mmol) TFA•Tyr-D-Ala-Phe-Gly-oBzl was dissolved in 150 ml DMF and to this was added 1.5 ml (13.0 mmol) of N-methyl morpholine. 5.2 g (14.6 mmol) Boc-Arg (NO$_2$)-OH•½ THF, 1.97 g (14.6 mmol) N-oxybenzotriazole was then added. The reaction was cooled to-10° C. with mixing and to this was added 3.0 g (14.0 mmol) dicyclohexyl carbodiimide. The reaction mixture was stirred for 3 days at room temperature. The dicyclocarbamide was filtered off, and the solvent was evaporated under vacuum. The residue was combined with 100 ml ethyl acetate, rinsed twice with 50 ml of 2% sulfuric acid solution, rinsed twice with 80 ml saturated sodium bicarbonate solution, rinsed with water to neutral pH, and dried over anhydrous sodium sulfate. The ethyl acetate layer was evaporated under vacuum. The residue was crystallized from ethyl acetate. The yield was 9.6 g (87.2%). The melting point was 176.7° C. $R_f$=0.70 in chloroform:ethyl acetate:methanol:acetic acid=6:3:1:0.5. $R_f$=0.23 in chloroform:methanol=9:1.

(e) Preparation of H-Arg-Tyr-D-Ala-Phe-Gly-OH 9.6 g (13.6 mmol) of Boc-Arg(NO$_2$)-Tyr-D-Ala-Phe-Gly-oBzl was dissolved in 60 ml formic acid. 1.0 g palladium catalyst was added, and hydrogen was passed through the solution for 6 hours. The catalyst was removed by filtration, and the formic acid was removed by evaporation under vacuum. 100 ml water was added to the resultant product, and the evaporation was repeated. The residue was combined with diethyl ether. The precipitate was separated by filtration, rinsed with ether and air-dried. The yield was 6.9 g (100%). $R_f$=0.44 in butanol: acetic acid:water=3:1:1.

The peptide was purified by ion exchange chromatography through a column packed with Sephadex G-25 in a gradient of 0.1 M–1.0 M pyridine acetate buffer solution.

The peptide H-Arg-Tyr-D-Ala-Phe-Gly-OH is a white or yellowish-white powder, soluble in water, slightly soluble in alcohol, and practically insoluble in chloroform. The peptide has a molecular weight of 612.6, and a linear structure.

The UV spectrum within 250–300 nm exhibits a maximum at 275±2 nm. A 0.1% water solution of the peptide has a pH of 5.7–7.0.

EXAMPLE 2
Preparation of H-Arg-Tyr-D-Orn-Phe-D-Ala-OH (a) Preparation of Z-Phe-D-Ala-OH 9.68 g (20.0 mmol) of Z-Phe-OPfp was dissolved in 20 ml of THF and to this was added 2.3 g (25.6 mmol) of H-D-Ala-OH dissolved in 5 ml water, pH 8.5. The reaction mixture was stirred for one day and one night at room temperature. The solvents were removed by evaporation under vacuum, 70 ml ethyl acetate was added, and the mixture was acidified to pH 2–3 by the addition of 70 ml of 2% sulfuric acid. The peptide was extracted twice with 70 ml ethyl acetate, washed with saturated sodium chloride solution to neutral pH, then dried over anhydrous sodium sulfate. The solvent was removed by evaporation under vacuum, leaving a thick oil. The product was crystallized from ether/hexane. The yield was 7.6 g (97.7%), melting point was 153–154° C. $R_f$=0.40 in chloroform:ethyl acetate-:methanol:acetic acid=6:3:1:0.1. $R_f$=0.53 in acetic acid:chloroform:methanol=0.5:16:1. $R_f$=0.58 in acetic acid:chloroform:methanol=0.5:9:1. $[\alpha]^{20}_D$=+3.2 (C=1, CH$_3$OH).

(b) Preparation of Boc-D-Orn(Z)-Phe-D-Ala-OH 6.5 g (18.0 mmol) of Z-Phe-D-Ala-OH was dissolved in 15 ml methanol and 2 ml formic acid. 0.2 g palladium catalyst was added and hydrogen was passed through the solution for 3 hours. The catalyst was removed by filtration, and the solvents were evaporated under vacuum. The residue was flooded with ether. The precipitate was filtered off, rinsed with ether and dried. The yield of H-Phe-D-Ala-OH was 5.3 g (98.1%). $R_f$=0.01 in chloroform:ethyl acetate-:methanol:acetic acid=6:3:1:0.1. $R_f$=0.45 in acetic acid:chloroform:methanol=1:3:2:2.

8.0 g (15.0 mmol) of pentafluorophenyl ester of Boc-D-Orn(Z)-OPfp was dissolved in 15 ml dioxane. To this was added with mixing 4.3 g (17.7 mmol) H-Phe-D-Ala-OH dissolved in water with pH 8.5. The reaction mixture was stirred for a day and a night at room temperature. The solvents were evaporated under vacuum, 70 ml ethyl acetate was added, and the mixture was acidified to pH 2–3 by the addition of 2% sulfuric acid solution. The peptide was extracted twice with 70 ml ethyl acetate, washed with saturated sodium chloride solution to neutral pH and dried over anhydrous sodium sulfate. The solvent was removed by evaporation under vacuum leaving a thick oil. The product was crystallized from ethyl acetate with ether and hexane. The yield was 6.92 g (74.4%), and the melting point was 145° C. $R_f$=0.44 in acetic acid:chloroform;methanol=0.5:16:1. $R_f$=0.32 in chloroform:ethyl acetate:methanol=6:3:1.

(c) Preparation of Boc-Tyr(Bzl)-D-Orn(Z)-Phe-D-Ala-OH 3.3 g (5.6 mmol) of Boc-D-Orn(Z)-Phe-D-Ala-OH was dissolved in 10 ml of 50% TFA in chloroform. After 1 hour the solvents were removed by evaporation under vacuum, and ether was added to the residue. The precipitate was filtered off, rinsed with ether and dried. The yield was 3.0 g (100%).

3.0 g (5.4 mmol) of Boc-Tyr(Bzl)-OPfp was dissolved in 10 ml DMF. To this was added 3.0 g (5.8 mmol) of TFA•H-D-Orn(Z)-Phe-D-Ala-OH and 0.25 ml (5.7 mmol) diethyl isopropyl amine. The reaction mixture was stirred for a day and a night at room temperature. The solvent was evaporated under vacuum, 70 ml ethyl acetate and 70 ml of 2% sulfuric acid was added to bring the pH to 2–3. The peptide was extracted twice with 70 ml ethyl acetate, washed to neutral pH with saturated sodium chloride solution and dried over anhydrous sodium sulfate. The solvent was removed by evaporation under vacuum leaving a thick oil. The product was crystallized from ethyl acetate and ether. The yield was 4.1 g (82.0%). $R_f$=0.47 in acetic acid:chloroform:methanol=0.5:16:1. $R_f$=0.35 in acetic acid:chloroform:methanol=0.5:16:1.

(d) Preparation of Z$_3$-Arg-Tyr(Bzl)-D-Orn(Z)-Phe-D-Ala-OH 0.9 g (1.1 mmol) of Boc-Tyr(Bzl)-D-Orn(Z)-Phe-D-Ala-OH was dissolved in 5 ml of 50% TFA in chloroform. After 1 hour the solvents were removed by evaporation under vacuum, and ether was added to the residue. The precipitate was separated by filtration, rinsed with ether and dried. The yield was 0.8 g (100%).

0.65 g (1.1 mmol) of Z$_3$-Arg-OPfp was dissolved in 5 ml dioxane and 1.5 ml DMF. To this was added 0.8 g (1.0 mmol) diethyl isopropyl amine. The reaction mixture was stirred for a day and a night at room temperature. The solvent was evaporated under vacuum, and ethyl acetate was added. The precipitate was separated by filtration. The product obtained was crystallized from ethyl acetate. The yield was 1.88 g (92.0%) and the melting point was 138–143° C. $R_f$=0.51 in acetic acid:chloroform:methanol=0.5:16:1. $R_f$=0.34 in chloroform:ethyl acetate:methanol:acetic acid=6:3:1:0.1. $R_f$=0.53 in acetic acid:chloroform:methanol=0.5:9:1.

(e) Preparation of H-Arg-Tyr-D-Orn-Phe-D-Ala-OH 0.5 g (0.39 mmol) of Z$_3$-Arg-Tyr(Bzl)-D-Orn(Z)-Phe-D-Ala-OH was dissolved in 3 ml acetic acid and 2 ml formic acid. 0.62 g palladium catalyst was added, and hydrogen was passed through the solution for 3 hours. The catalyst was removed by filtration, and the solvents were removed by evaporation under vacuum. The product was dissolved in water and purified by reverse phase HPLC through a 1.6×25 cm column packed with Silasorb C-18 (10 μm) in acetonitrile—0.01 M triethylammonium acetate (pH=6.0). The yield was 0.20 g (80.8%).

EXAMPLE 3

Preparation of H-Arg-Tyr-D-Arg-Phe-D-Ala-OH 0.09 g (0.14 mmol) of H-Arg-Tyr-D-Orn-Phe-D-Ala-OH was guanidilled by dissolution in 5 ml of 1 M solution of o-methyl isocarbamide, and the pH was adjusted to 11.05 with 1N sodium hydroxide solution. The reaction mixture was stirred for 7 days at room temperature and purified by reverse phase HPLC through a 1.5×25 cm column packed with Silasorb C-8 (10 μm) in a gradient of acetonitrile—0.05% TFA. The yield was 0.087 g (76.9%).

EXAMPLE 4

Preparation of H-Tyr-D-Orn-Phe-D-Glu-OH (a) Preparation of Boc-Phe-D-Glu-(oBzl)$_2$ 14.7 g (10.0 mmol) of H-D-Glu-OH was dissolved in 54 ml benzyl alcohol and 17.2 g (10.0 mmol) of p-toluene sulfoacid was added. The mixture was heated to 70–80° C. in a Din-Stark apparatus for 12 hours. During the reaction, benzene was added as water was removed. The product obtained was crystallized from methanol and recrystallized from isopropanol. The yield of TOS•H-D-Glu-(oBzl)$_2$ was 26.96 g (80.0%), and the melting point was 116° C.

2.2 g (5.1 mmol) of Boc•Phe-OPfp was dissolved in 5 ml dioxane and added with mixing to a solution of 1.9 g (5.2 mmol) TOS•H-D-Glu(oBzl)$_2$ and 0.5 ml (5.2 mmol) triethyl amine in 5 ml methylene chloride and 5 ml dioxane. The reaction mixture was stirred for a day and a night at room temperature. The solvent was evaporated under vacuum. The oily residue was dissolved in 100 ml of ethyl acetate, washed twice with 100 ml of 2% sulfuric acid, washed twice with 100 ml 5% sodium bicarbonate solution, then washed with water to neutral pH, and dried over anhydrous sodium sulfate. The ethyl acetate was removed by evaporation under vacuum. The residue was crystallized from ethyl acetate-hexane. The yield was 3.2 g (98.5%), and the melting point was 162° C. $R_f$=0.81 in chloroform:ethyl acetate:methanol=6:3:1. $R_f$=0.78 in acetic acid: chloroform:methanol=0.5:16:1.

(b) Preparation of Boc-D-Orn(Z)-Phe-D-Glu-(oBzl)$_2$ 2.1 g (3.7 mmol) of Boc-Phe-D-Glu(oBzl)$_2$ was dissolved in 20 ml of 50% TFA in chloroform. After 1 hour, the solvents were removed by evaporation under vacuum. The residue was dissolved in 10 ml THF, and to this was added 0.4 ml diethyl isopropyl amine and 2.0 g (3.8 mmol) of Boc-D-Orn(Z)-OPfp. The reaction mixture was stirred for a day and a night at room temperature. The solvent was evaporated under vacuum. The oily residue was dissolved in 100 ml ethyl acetate, washed twice with 100 ml of 2% sulfuric acid, washed twice with 100 of 5% sodium bicarbonate solution, washed with water to neutral pH, and dried over anhydrous sodium sulfate. The ethyl acetate was removed by evaporation under vacuum. The residue was crystallized from ethyl acetate-ether-hexane. The yield was 3.0 g (88.2%), and the melting point was 156° C. $R_f$=0.88 in chloroform:ethyl acetate:methanol=6:3:1. $R_f$=0.85 in acetic acid chloroform:methanol=0.5:9:1.

(c) Preparation of Boc-Tyr(Bzl)-D-Orn(Z)-Phe-D-Glu-(oBzl)$_2$ 0.91 g (1.1 mmol) of Boc-D-Orn(Z)-Phe-D-Glu(oBzl)$_2$ was dissolved in 10 ml of 50% TFA in chloroform. After 1 hour, the solvents were removed by evaporation under vacuum. The residue was dissolved in 15 ml dioxane, and to this was added 0.10 ml diethyl isopropyl amine and 0.54 g (1.0 mmol) of Boc-Tyr(Bzl)-oPfp. The reaction mixture was stirred for a day and a night at room temperature. The solvent was evaporated under vacuum. The oily residue was dissolved in 100 ml ethyl acetate, washed twice with 100 ml 2% of sulfuric acid, washed twice with 100 ml 5% sodium bicarbonate solution, washed with water to neutral pH, and dried over anhydrous sodium sulfate. The ethyl acetate was removed by evaporation under vacuum. The residue was crystallized from ethyl acetate-ether. The yield was 1.1 g (93.2%) and the melting point was 158–160° C. $R_f$=0.89 in chloroform:ethyl acetate:methanol=6:3:1. $R_f$=0.83 in acetic acid:chloroform:methanol=0.5:16:1.

(d) Preparation of H-Tyr-D-Orn-Phe-D-Glu-OH 0.16 g (0.15 mmol) Boc-Tyr(Bzl)-D-Orn(Z)-Phe-D-Glu-(oBzl)$_2$ was dissolved in 2 ml methanol. To this was added 2 ml formic acid and 0.2 g palladium catalyst, and hydrogen was passed through the solution for 4 hours. The catalyst was removed by filtration, and the solvents were removed by evaporation under vacuum. The oily residue was dissolved in 5 ml of 70% TFA in water. After 1 hour, the solvents were removed by evaporation under vacuum. The product was dissolved in minimum methanol, diluted with water, and purified by reverse phase HPLC through a 1.6×25 cm column packed with Silasorb C-8 (10 μm) under gradient conditions of acetonitrile—0.05% TFA. The yield was 0.07 g (98.8%).

EXAMPLE 5

Table 1 presents physical and chemical characteristics of some derivatives of the peptide (general structure I): $R_{fA}$ in the system (butanol:acetic acid:water=3:1:1), $R_{fB}$ in the system (chloroform:methanol: 32% acetic acid=60:45:20) and $[alpha]^{20}_D$.

Biological studies of the claimed peptide showed its comprehensive action. The peptide proved to be non-toxic. The peptide toxicity (LD$_{50}$) was studied in 24 white mice weighing 18 g. The animals received the same diet and were kept in the same conditions. Half of the animals in each group were male mice and the other half were female mice. Twenty-four hours before the experiment and during it, the animals were housed in a vivarium with a constant temperature and ventilation. Two hours before the experiment the animals were deprived of water and food. The animals were divided into four groups, 6 mice each. Mice of groups 1, 2 and 3 were injected intraperitoneally with 0.2 ml of water solution of the peptide in the dose of 800, 1100 and 1400 mg/kg, respectively. Control animals (group 4) were injected with the same volume of physiological solution. The observation period lasted 7 days after the injections, then LD$_{50}$ was calculated. No changes were observed in the animals' general state or behaviour both immediately after injections and throughout the observation period. The peptide injections did not cause pain syndromes. No animals died in the period. The animals had normal weight gains, weight factors of the organs varied within the physiological norm.

The results of the study showed that intraperitoneal injections of the peptide in the doses of 800, 1100 and 1400 mg/kg did not cause any toxic effect and even high doses of the peptide were well tolerated by the animals.

EXAMPLE 6

The peptide was tested for its opioid and analgesic effects. The opioid activity was studied using in vitro tests in isolated organs: GPI test (Guang, T. A., Kosterlitz, H. W; Agonist and Antagonist Action of Morphine-Like Drugs on Guinea-Pig Isolated Ileum, Br. J. Pharmacol. Chmother, 1966, vol. 27, no. 3, pp 514–527) and MVD test (Hughes J., Kosterlitz H. W., Leslie F. M., Effect of Morphine on Adrenergic Transmission in the Mouse Vas Deferens. Assessment of Agonist and Antagonist Potencies of Narcotic, Br. J. Pharmacol., 1975, vol. 53, no. 3, pp. 371–381). In addition, opioid activity was studied in analgesic tests in vivo: "hot plate" test (Aukier S. I., New Hot Plate Test to Qualify Antinociceptive and Narcotic Antagonist Activities, Eur. J. Pharmacol., 1974, vol. 27, no. 1, pp. 1–4) and "tail flick" (D'Amour F. E., Smith D. L. A Method for Determining Loss Exp.Ther.-1974-v.72,N1, p.74–79) in rats.

The "tail flick" method was used to test the analgesic activity of a number of peptides administered intranasally, in a dose of 0.005 mg per kg body weight. Significant analgesia, 242 U, was demonstrated by the peptide H-Arg-Tyr-D-Ala-Phe-Gly-OH (herein also referred to as "Sedatin").

The results of the opioid studies for some of the peptides of the present invention are shown in Table 2. The minimal biologically effective dose of the peptides was found to be 1–10 μg per Kg of body weight.

EXAMPLE 7

The effect of the peptide on morphological changes in skin and hair integument was studied.

The tests were performed in 4 groups of NMRI mice. Group 1 was a control, and groups 2, 3 and 4 received a Sedatin preparation with drinking water in the doses of 1.0, 10.0 and 100.0 gg per kg body weight, respectively.

Skin samples, 5 mm×5 mm, were taken by biopsy from the withers area, and fixed for 48 hours according to Lilly. The samples were then rinsed in alcohols of descending battery and immersed into Hemolaun-Mayer dye for 24 hours. Histological preparations were made by using Reichard microtone. Skin pieces were oriented in the plane of the axial hair growth and sections were stained with eosin by classic methods.

Histological preparations 10 μm thick were examined for the quality of epidermis and derma. The number of hair follicles per 1 mm$^2$ was counted according to Aftandilov in the control and test mice. It was found that the number of hair follicles in mice receiving 100.00, 10.0 and 1.0 μg per kg body weight was 14%, 19% and 22% more than in the control group, respectively.

Skin section examinations revealed epidermal layer growth with a considerable hyperkeratinization in mice of group 4 (which were administered 100 μg of the peptide per Kg of body weight). Changes in group 3 were similar to those for group 4, with areas of epidermal thickening being observed. In group 2 the epithelium growth zone was more active, and the subcutaneous fatty cellular tissue was in a better condition as compared with the control.

The hair length withers was assessed. The lengths of 10 hairs of each mice were measured to a micron, and mean values were calculated for each group. The results are shown in Table 3. It is evident that mice which were administered doses of 10 and 100 µg per kg body weight of the peptide showed increased hair growth over the control group.

EXAMPLE 8

The effect of the peptide on the weight gain in young mice and rats was studied.

Four groups of 1-month old white mongrel rats were compared. Group 1 was the control group, and received injections of 0.1 ml of physiological solution. Test Groups 2, 3 and 4 received intraperitoneal injections of the Sedatin in doses of 0.1, 0.5 and 1.0 µg per kg of body weight. The rats of all groups were weighted every 5 days, and food consumption was recorded. The experiment lasted 35 days. The results are shown in Table 4 ($p<0.05$). The group which received 1.0 µg of the peptide per kg of body weight showed the largest weight gain (group 4). Table 5 shows the food consumption of the rats. There was no significant deviation in food consumption in the different groups.

Seven groups of 1-month old NMRI mice were compared. Food and water were available to the mice as desired. Group 1 was the control group and was administered injections of 1.0 ml of physiological solution. Test Groups 2, 3, and 4 were given the peptide with drinking water in the amounts of 1.0, 10.0, 100.0 µg per kg body weight, respectively. Test Groups 5, 6, and 7 received daily intraperitoneal injections of 0.1 ml of the peptide water solution containing 0.1, 0.5 and 1.0 µg of the peptide per kg of body weight, respectively. The test lasted 30 days. The mice were weighted twice per week, and food consumption was measured daily.

The weight changes in the mice are shown in Table 6. Oral administration of the peptide in a dose of 0.1 µg with drinking water produced the largest weight gain.

Table 7 shows the average daily food consumption of the mice. Mice receiving the peptide with drinking water in an amount of 1.0 µg per kg body weight (i.e. those with the largest weight gain) consumed more food.

As peptide administration changes both weight gain and food consumption, weight gain expressed in percent per 1 g of consumed food was calculated. This characterized the profitability of the use of the peptide. The results are shown in Table 8. The maximum weight gain per consumption of 1 g of food was in the group which received 10 µg of the peptide per kg body weight through drinking water (i.e. 36.5% more than in the control group).

EXAMPLE 9

The effect of the peptide on weight gain in chickens was examined. Tests were conducted on chickens of egg oriented productivity, "P-46" breed. 24 hour old cockerels were divided in 5 groups, 13 cockerels in each—one control group and 4 test groups. The cockerels in the test groups were given Sedatin mixed with feed in the amounts shown in Table 9.

The birds were given a full diet till they reached the age of 10 weeks. 100% of birds in both the control and test groups survived. Observations showed that the tested cockerels willingly ate the feed containing the peptide, and the appearance of the test cockerels did not differ from the control group.

The average day's weight gain in the test groups 3–5 was 13–23% higher than those in the control group. As a result, for the test cockerels, feed consumption per 1 kg of weight gain was lower than those in the control group.

After 10 weeks, the cockerels were killed and examined. The examination showed that the weight of eviscerated and semieviscerated cockerels was higher in the test groups which were administered the peptide, than those in the control group. The results are shown in Table 9 and FIG. 1. As can be seen, the highest weight increase was observed in the group 3 cockerels, which were administered 12 µg of the peptide per day.

Quality of the cockerel meat was tested on an organoleptic basis. The tests showed that in all groups, the colour, smell, consistency and taste of meat was the same as in the control group.

EXAMPLE 10

The effects of the peptide on minks and arctic foxes were examined. The study was carried out in 2-month old minks and arctic foxes. Each species of animal was divided into 3 test groups and 1 control group. Minks were divided into groups each containing 25 female and 25 male minks. There were 10 males and 10 females in each group of arctic foxes.

The animals were administered Sedatin which was well mixed with their feed according to the following scheme. The first group was administered Sedatin each day, in a dose of 10 µg per 1 kg of body weight. The second test group was administered the peptide in a dose of 10 µg per 1 kg of body weight for a period of ten days, then no peptide was administered during the following ten days; this regimen was repeated for the duration of the experiment. The third test group was administered the peptide according to the same scheme as the second test group, but the dose was 20 µg per 1 kg of weight. The control group was not administered any peptide during the experiment. The minks and arctic foxes were kept in ordinary sheds, 2 animals in each.

Figure 2:
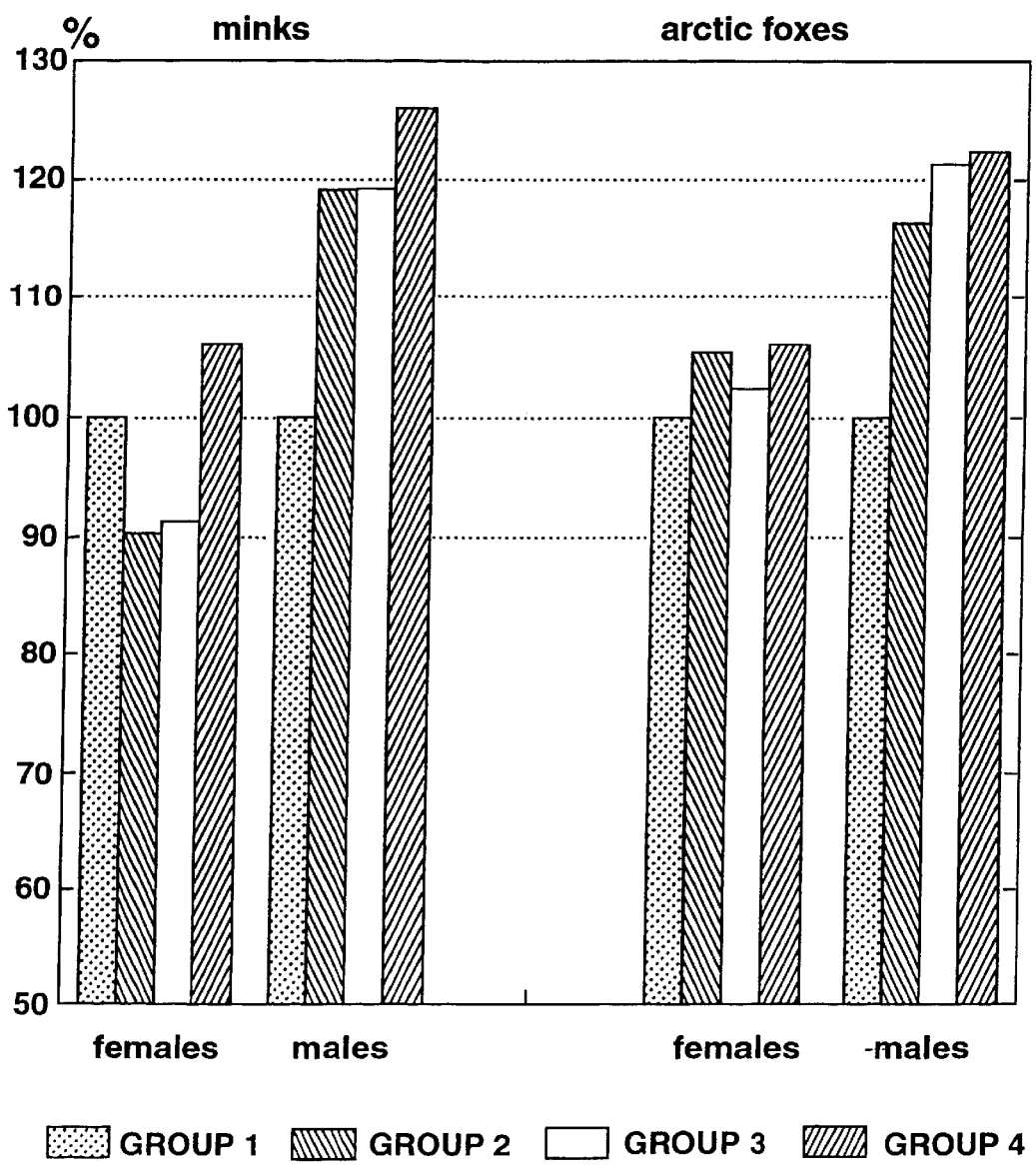
FIG. 2 is a graph showing the weight gain in mink and arctic foxes administered a peptide in accordance with the present invention compared with a control group.

One month after commencing the experiment, the animals were weighed. The difference in weight was registered for male minks and male and female arctic foxes compared to the weight of animals in control groups. The results are shown in FIG. 2 and Table 10 (mean values with deviation limits calculated using student's T-test). Weight gains in female minks and arctic foxes of Group 4 (20 µg per kg body weight) were 6%, and in males 26% and 21% respectively. Thus, the animals administered a dose of 20 µg per 1 kg of body weight showed the largest increase in weight, for both male and females of both the minks and arctic foxes.

Figure 3:
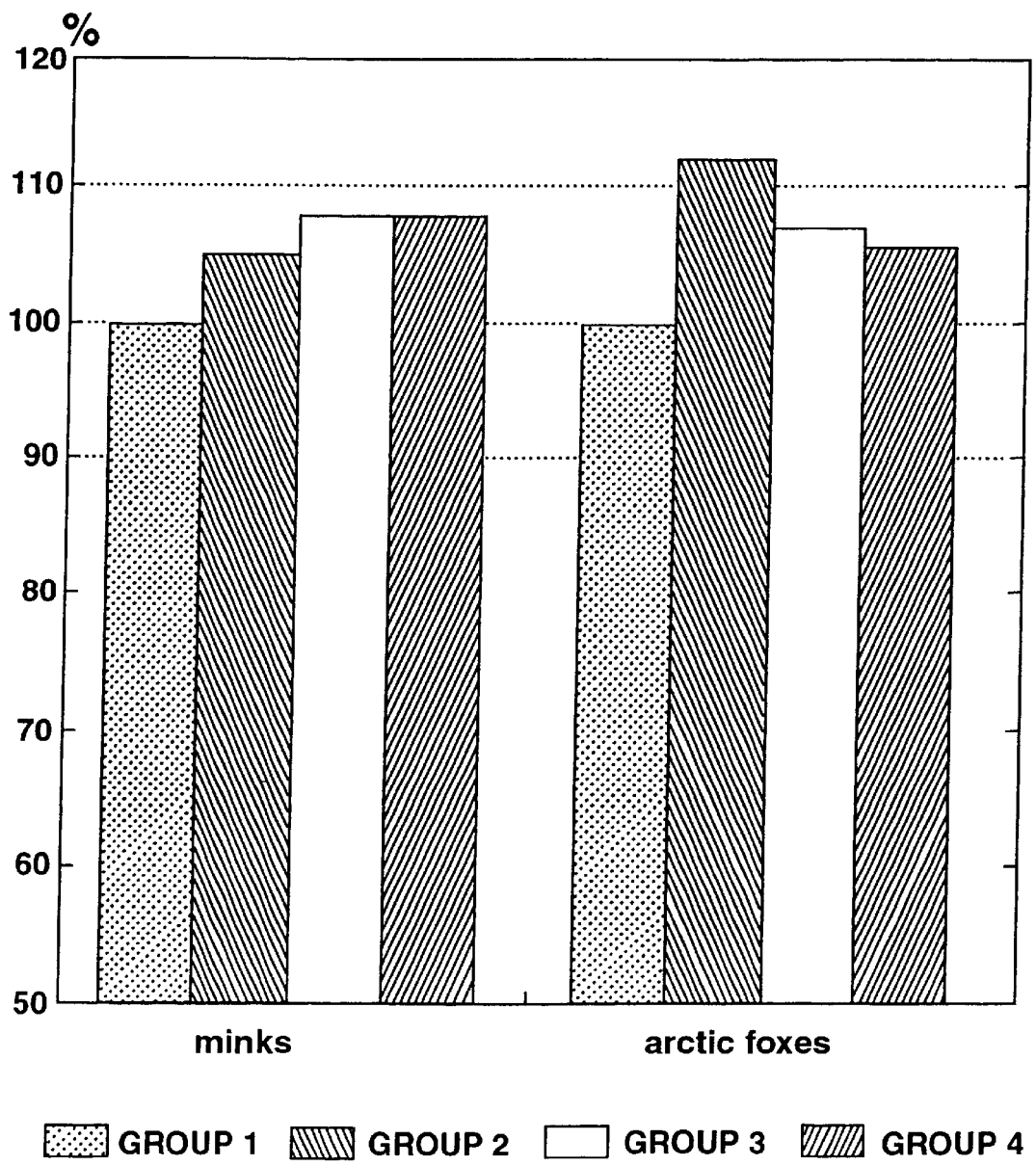
FIG. 3 is a graph showing the skin area in mink and arctic foxes administered a peptide in accordance with the present invention compared with a control group.

At the end of experiment the animals were killed. Then the pelts were examined and their area was measured. The area of skin present in the test groups of minks and arctic foxes was larger than in the control groups respectively. For minks, the area was on the average 7.9% larger for the second and third test groups (Groups 3 and 4); for arctic foxes it was 12.3% larger in the first test group. The results are shown in FIG. 3. The quality characteristics of the pelts were the same.

EXAMPLE 11

The effect of the peptide on pigs was tested. The test was conducted in two stages, as discussed below.

The purpose of the first stage of testing was to determine the optimal dose of the peptide necessary to achieve the desired weight gain and the most beneficial manner of administering the peptide. The first stage of testing was conducted over a period of 100 days.

The pigs were divided into seven groups of ten animals each. The animals were all aged 4–5 months, and weighed about the same. There was one control group and six test groups. All the groups were given an ordinary diet. The first 3 test groups were administered Sedatin together with feed, in the amounts shown in Table 11.

Test groups 2, 3, and 4 were administered the peptide (1.0, 5.0, 10.0 µg kg/body weight) with feed, for 20 days each month with a 10 day break. Test groups 5, 6, and 7 were administered the peptide by injections of 0.01% water solutions for five days each month with a 25 day break (0.1, 0.5 and 1.0 µg per body weight).

Figure 4:
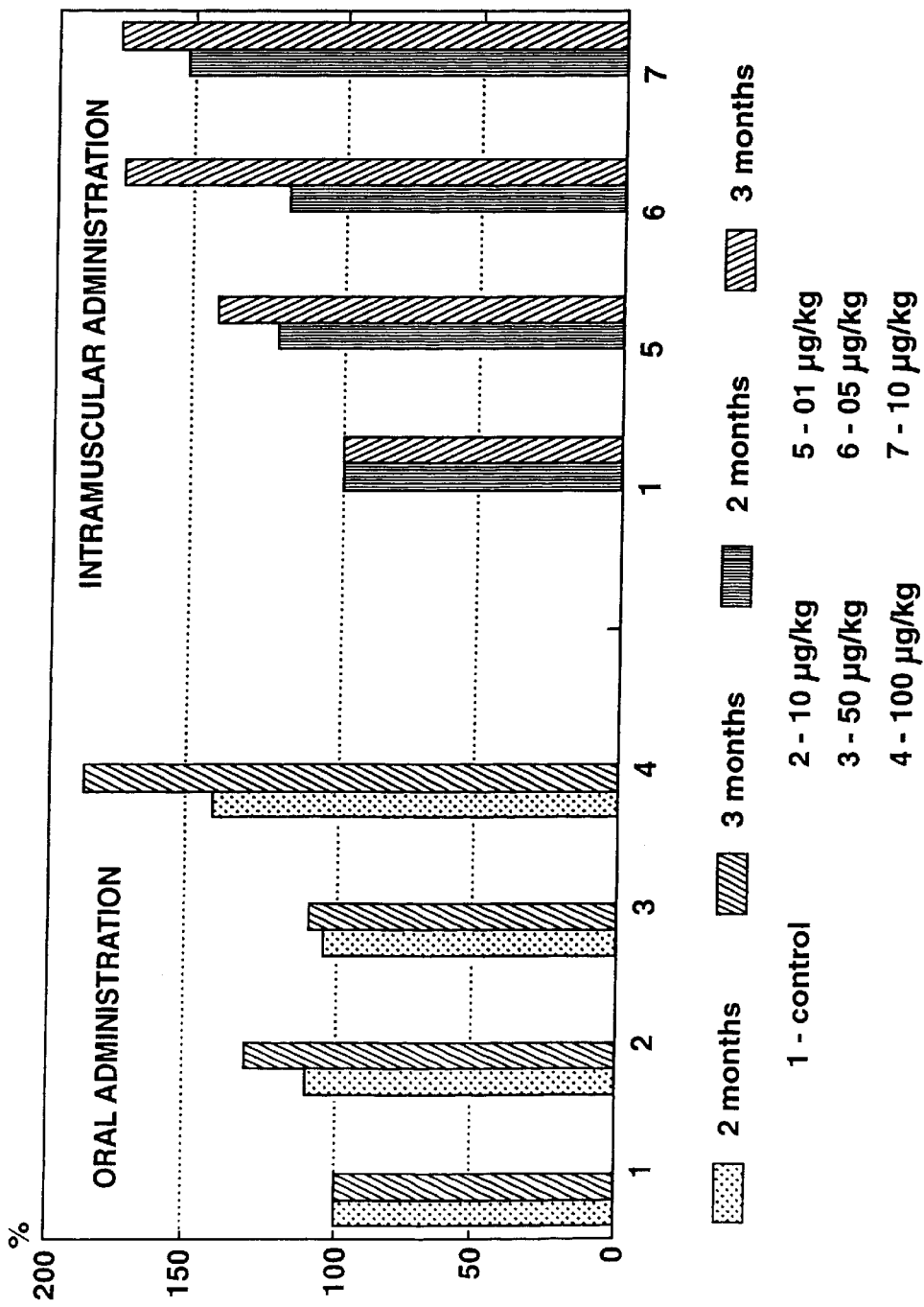
FIG. 4 is a graph showing the weight gain in pigs administered a peptide in accordance with the present invention compared with a control group.

Physiological examinations and biochemical tests were carried out during the experiment. The pigs were weighed on the 30th, 65th and 100th days of the experiment. The results are shown in Table 11 and FIG. 4. The results showed that the largest weight gain was achieved with the higher doses of the peptide. The animals in the third group which received the peptide together with feed (oral administration) in a dose of 10 µg per 1 kg of body weight showed a weight gain 30% higher than in the control group. Administration of 1 µg per 1 kg of body weight by intramuscular injections achieved a weight gain 18% higher than the control group (group 6).

Figure 5:
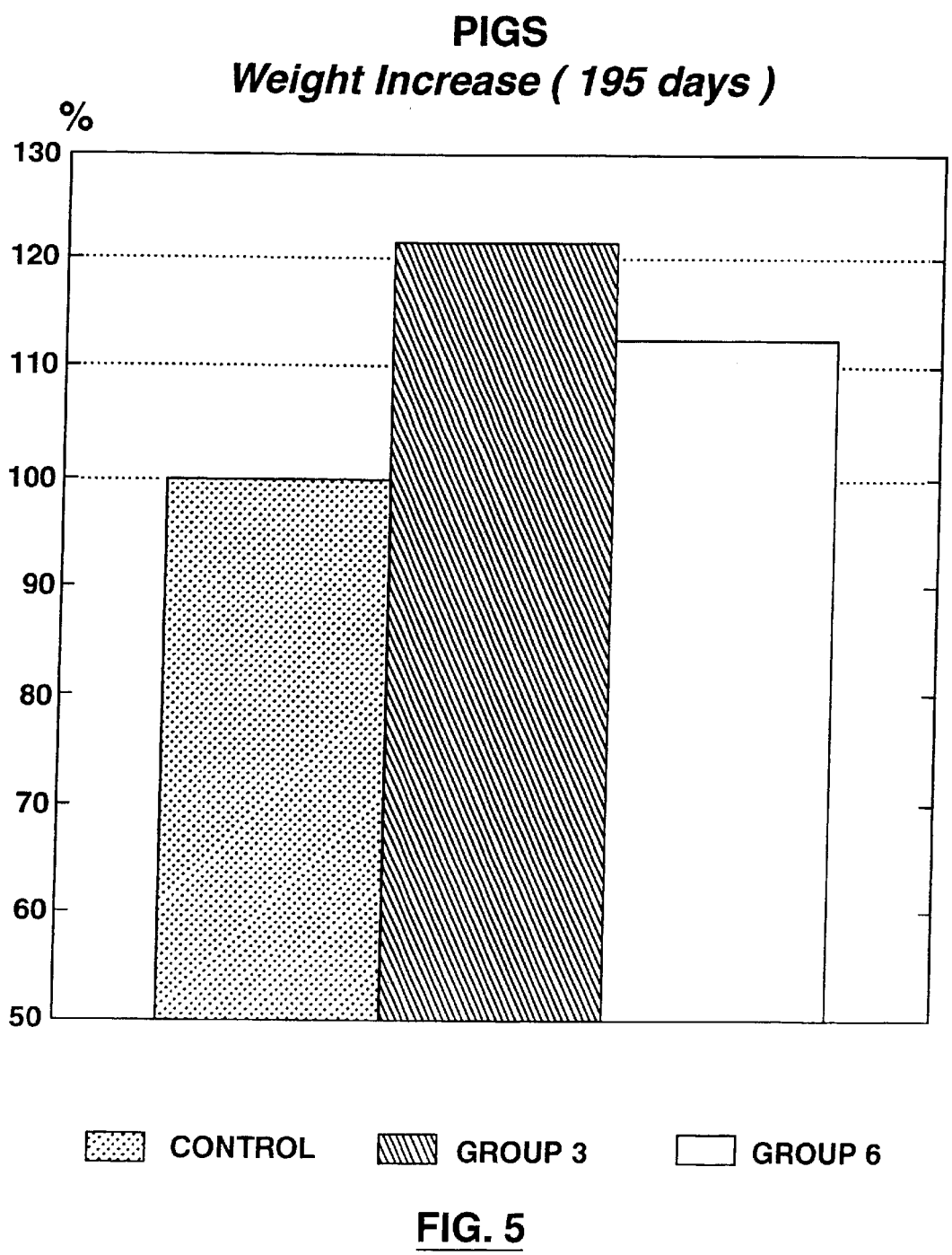
FIG. 5 is a graph showing the weight gain in pigs orally administered a peptide in accordance with the present invention orally compared with administration of the peptide by intramuscular injection.

The second stage of the experiment lasted 95 days, after which the animals were killed. The second stage of the experiment was carried out only with groups three and six, in order to determine which method of administration of the peptide produced the best results. To eliminate undesirable effects, the animals were not weighed before killing. The results are shown in FIG. 5. It will be seen that the best effect was achieved in group three where the peptide was dissolved in water and mixed with the animal feed.

During the entire 195 days of the experiment, weight gain in group three was 621.5 g, or in other words, it was 46.1 g higher than in group six, and 108.5 g higher than in the control group.

Besides quantity characteristics, quality characteristics were examined. No changes were observed, for example, in pathological changes, decrease of fat layer, etc. Different biochemical and physicochemical tests were carried out which showed no deviation from the control group.

EXAMPLE 12

The effect of the peptide was studied on young bulls.

There were 7 groups of animals having approximately the same weight, with 12 young bulls in each group. The age of the animals was 2 months. There were 6 test groups and one control. The test animals were administered Sedatin with water before they were fed or as intramuscular injections in the amounts shown in Table 12. All animals received the same diet and were kept in the same conditions. Two animals in the control group fell ill during the experiment, and were replaced by analogs.

During the experiment the temperature, pulse and breath-rate were monitored and no deviation from the control group was observed.

Figure 6:
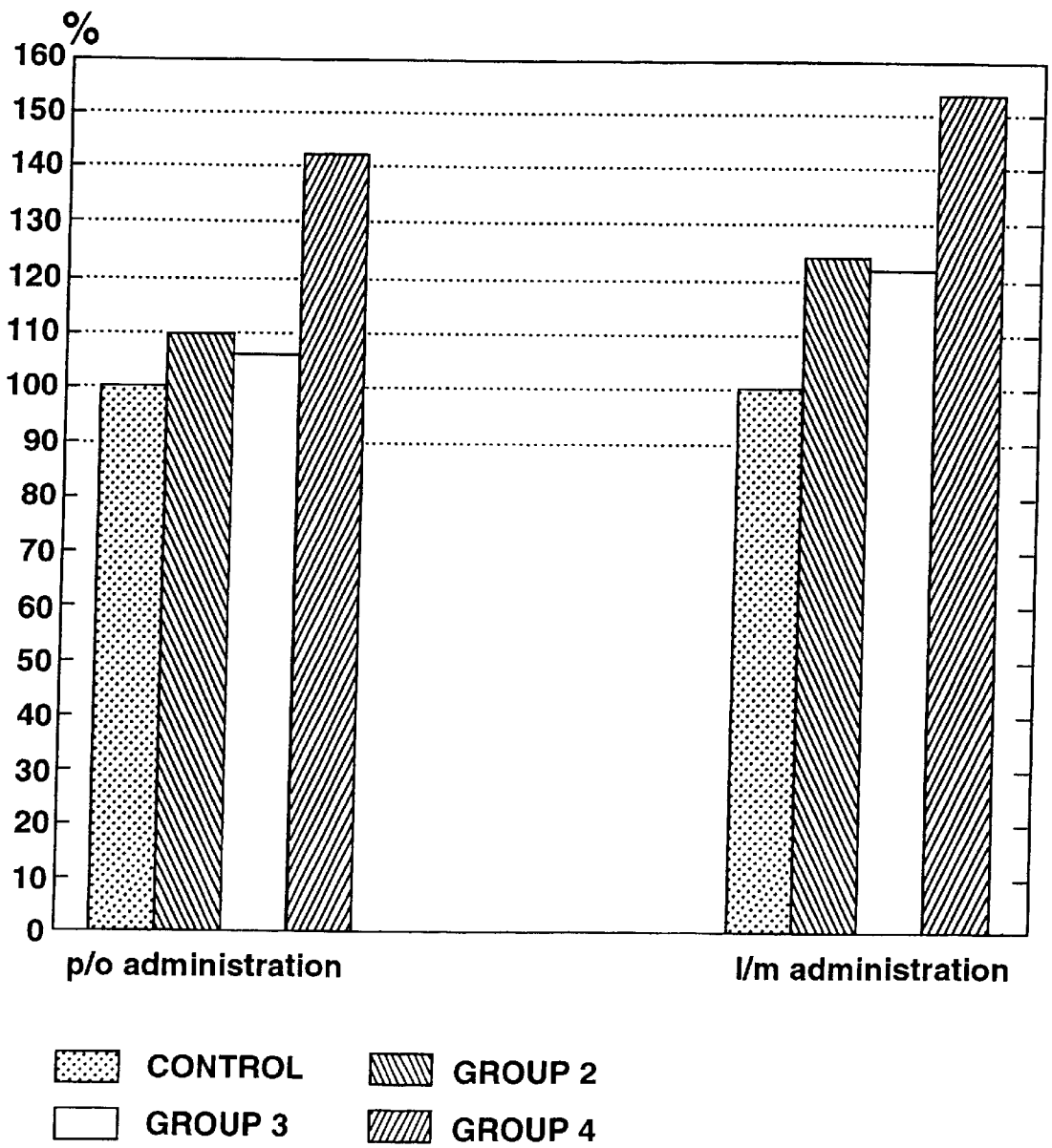
FIG. 6 is a graph showing the weight gain in bulls administered a peptide in accordance with the present invention compared with a control group.

The results of the experiment showed that the peptide has a positive effect on weight gain in young bulls, for both methods of administration of the peptide. The largest weight gain was observed in animals which were administered the largest dose of the peptide. Group four, in which the young bulls were administered the peptide dissolved in water (10 µg per 1 kg of body weight), showed an average daily weight gain of 582 g during a 60 day period, or 172 g higher than the animals in the control group. When the peptide was administered by intramuscular injection (the dose being 1 µg per 1 kg of body weight), an even larger average daily weight gain was observed, i.e. 627 g, or 217 g higher than in the control group. The results are shown in FIG. 6 and Table 12.

Two groups, one control and one test, were chosen for the second stage of the experiment. The test group was administered the peptide mixed with feed, in the amount of 10 µg per 1 kg of body weight. The control group was not administered any of the peptide. The experiment lasted 30 days, and the results are shown in Table 13. The data was biometrically processed. It will be seen that the bulls which were administered the peptide showed an increased average daily weight gain compared with the control group.

EXAMPLE 13

The effect of the peptide was studied in carp and trout. The tests were performed at different periods of fish growth: for roe, larvas, hutchlings and yearlings, with different methods of administration being applied. Mongrel guppies were used as a model object.

Conventional methods of administration to fish, allowing large scale treatment, include the introduction of a preparation into artificial feed and immersion in solution. Thus, Sedatin was dissolved in water to obtain solutions of various concentrations of the peptide.

The roe of coast rainbow trout was delivered in a thermoplastatic foam box to the laboratory. The roe was incubated in Petri dishes containing 30 ml of water. Initially, the number of fish eggs or larvae was 25 per dish. Guppies were held in flat crystallizers with water being changed regularly. The fish were fed with the salmon feed. The density was 10 fish per liter of water.

During the experiments carp were kept in suitable tanks allowing water recirculation and regeneration. Hematological and morphophysiological tests were carried out according to conventional procedures. The results were statistically processed.

A. Effect on Growth of Carp

The carp were maintained in aquariums. Ten carp were administered Sedatin for 2 hours in a concentration of 0.25 mg/l of water. The fish were marked, weighed and placed into a recirculating aquarium system. The fish daily received dry granular feed for carps in the amount of 3% of the initial body weight. Twenty days later, all the fish were weighed. The results are shown in Table 14.

On average, the fish administered with the peptide showed a weight increase 23% larger than those in the control group, with individual weight increases ranging from 18.9 to 31.0% larger than those in the control group.

B. Effect on Growth of Trout

The effect of Sedatin on young trout was examined. The fish had an average initial weight of 0.5 g. The fish were divided into two groups, one test group and one control group. The test group fish were treated by immersion in a solution of the peptide having a concentration of 1.0 mg/l. It was found that by the end of the study the average weight of trout hutchlings was 2.83 g in the control group, and 3.86 g in the test group. Thus, the test group showed a weight increase 36.4% higher compared with the control group.

C. Effect on Caudal Fin Regeneration

The effect of Sedatin on the regeneration of caudal fins in trout was examined. The fish were divided into two groups; one control group and one test group. The test group were treated for 2 months by immersion in peptide solution containing 1.0 mg peptide per liter. The caudal fins of the fish were cut and the regeneration of the caudal fin was observed. A marked regeneration of caudal fins was observed in the fish administered the peptide, as compared with the control group. Measurement of the regeneration zone length (in mm) of the young trout caudal fins showed that the zone was 1.83±0.23 mm long in the control, and 2.86±0.26 mm long, i.e. almost 1.5 times longer in the test group compared with the control group. In carps, caudal fin regeneration was also 1.5 times longer than in the controls.

D. Effect on Immune Characteristics in Carp

Agglutinins are specific blood factors causing agglutination and neutralization of foreign particles and cells that get into an organism. After a week of treatment with Sedatin, the agglutination titer to rabbit erythrocytes in carp blood serum was 1.95 times larger than at the start of the experiment. The titer growth shows that the peptide considerably improved the organism reactivity and the fish became more resistant to protozoan and bacterial infections. As well, lysozyme activity was reduced by nearly 20%.

EXAMPLE 14

The ability of the peptide Arg-Tyr-D-Ala-Phe-Gly to reduce stress was examined.

(a) Preparation of Composition

To obtain a prolonged-release medicinal form suitable for parenteral administration, 1 weighed portion of the Arg-Tyr-D-Ala-Phe-Gly peptide is dissolved in 1 weighed portion of dimethyl sulfoxide. The solution is then diluted with 98 portions of polyethylene oxide-400. The resultant solution is used in the tests.

To obtain a prolonged-release medicinal form suitable for parenteral administration, 1 weighed portion of the Arg-Tyr-D-Ala-Phe-Gly peptide is dissolved in 10 weighed portions of dimethyl sulfoxide. The solution is then diluted with 89 portions of olive oil. The resulting solution is used in the tests.

(b) Evaluation of the Stress-corrective Effect of the Medicinal Form under an 18-hour Immobilization.

The test was conducted in triplicate, on 800 white Wistar rats at a temperature of 22–24° C. and a humidity of 80%. The preparation was administered as a single injection, subcutaneously. Control animals were injected with the same volumes of water. Rats received the peptide doses of 10.0 and 100.0 µg/kg before the main feeding; the medicinal form was prepared as described in example 1. Immediately following the compound injection, the rats were weighed and tied, lying on their backs, by their limbs to special boards for 18 hours. After the time had passed, the rats were untied, weighed and decapitated. During autopsy preparations were made of the thymus, adrenal glands, spleen and the stomach. The latter was examined for ulcers in the mucosa. Weight coefficients of the internals were calculated:

$$\text{Weight coefficient} = \frac{\text{Organ weight (mg or g)}}{\text{Body weight (g or kg)}}$$

The results of the tests are given in Tables 15–17.

As evident from Tables 15–17, the preparation inhibits body weight loss, guards against the stomach ulceration, prevents the hypertrophy of the adrenal glands and involution of the spleen and the thymus. This is indicative of its adaptogenic stress-corrective effect under the immobilization stress.

(c) Evaluation of the Stress-corrective Effect of the Preparation under Mental-and-exercise Stress.

The tests were conducted in duplicate on C57 Black mice at a temperature of 22–24° C. and humidity of 80%. The preparation was subcutaneously injected in single doses of 1.0, 10.0, 100.0, 1,000 µg/kg; the medicinal form was prepared as described in (a). Control animals were injected with the same volumes of water. The mice were subjected to a mental-and-exercise stress (swimming without load at a temperature 20° C. until being completely exhausted) one hour after the preparation injection. The results of the tests are presented in Table 18.

As one can see from Table 18, the use of the preparation extends the swimming duration by 11 to 50% after the first swimming, with the effect being dose-related. A considerable favorable stress-corrective effect is also seen during the repeated swimming, three hours after the first one. Twenty-four hours after the first swimming, the duration of the test mice swimming lengthened by 40 to 206% as compared to control animals that did not receive the preparation.

The adaptogenic stress-corrective activity of the preparation was also evaluated under mental-and-exercise stress with additional unfavorable effects. The test conditions differed from those described above as follows: the animals were made to swim at the temperature of +15° C. (hypothermia) and at +40° C. (hyperthermia). The mice were made to swim one hour following the preparation injection in accordance with the schedule similar to that described above, then 3 hours, and again 24 hours after the first swimming. The results are shown in Table 19.

As one can see from Table 19, despite the very small doses, the preparation protects animals against the combined mental and physical effect, increasing their tolerance to stress factors under hypothermia by more than 20%. Under hyperthermia, the animals tolerated the combined stress by 36.9% better even 24 hours after the preparation administration in the dose of 100 µg/kg body weight, which fact shows a sufficient adaptogenic stress-corrective effect of the claimed preparation.

EXAMPLE 15

The effect of the preparation on the development of narcotic sleep in mice.

The study was performed on 16 gray female mice at the ambient temperature of 20–22° C. and humidity of 80%. The preparation was injected subcutaneouly 1 hour prior to narcotic administration, in single doses of 1.0, 10.0, 100.0 µg per kg body weight in the form of 0.01% water solution. Control animals received water injections. One hour following the preparation injection, the animals were subcutaneouly injected with a water solution of sodium diethyl barbiturate (Medinal). Using a stop-watch, the narcotic asleep time, sleep time, and the time of awakening has been recorded. The obtained data were compared to control, the findings are summarized in Tables 20 and 21.

According to the data in Tables 20 and 21, the preparation lengthened the sleep time of narcotic-induced sleep by 10–20% and increases the survival rate of the animals injected with the maximal narcotic dose by 25% to over 200%.

Examples 14 and 15 demonstrate that the peptide of the formula Arg-Tyr-D-Ala-Phe-Gly is an efficacious adaptogen stress-corrector that can protect animals against physical, mental and chemical factors of the environment. The positive effect of a single injection of a µg-dose of the preparation can be still observed 24 hours after the administration.

Having illustrated and described the principles of the invention in a preferred embodiment, it should be appreciated to those skilled in the art that the invention can be modified in arrangement and detail without departure from such principles. We claim all modifications coming within the scope of the following claims.

All publications, patents and patent applications referred to herein are incorporated by reference in their entirety to the same extent as if each individual publication, patent or patent application was specifically and individually indicated to be incorporated by reference in its entirety.

TABLE 1

| 1 | $R_{fA}$ 2 | $R_{fB}$ 3 | $[\alpha]_D^{20}$ c = 1, 10% AcOH 4 |
|---|---|---|---|
| H-Arg-Tyr-D-Ala-Phe-Gly-OH | 0.54 | 0.71 | +43.0 |
| H-Arg-Tyr-D-Orn-Phe-Gly-OH | 0.19 | 0.25 | +36.2 |
| H-Arg-Tyr-D-Ala-Phe-D-Ala-OH | 0.56 | 0.75 | +47.0 |
| H-Arg-Tyr-D-Orn-Phe-D-Ala-OH | 0.16 | 0.74 | +10.0 |
| H-Arg-Tyr-D-Arg-Phe-D-Ala-OH | 0.18 | 0.30 | +43.8 |
| H-Arg-Tyr-D-Arg-Phe-D-Ala-NH$_2$ | 0.52 | 0.83 | +40.7 |
| H-D-Arg-Tyr-D-Arg-Phe-D-Ala-NH$_2$ | 0.52 | 0.83 | +5.0 |
| H-Orn-Tyr-D-Ala-Phe-D-Ala-OH | 0.58 | 0.81 | +36.0 |
| H-D-Orn-Tyr-D-Ala-Phe-D-Ala-OH | 0.52 | 0.83 | +5.0 |
| H-Lys-Tyr-D-Lys-Phe-Gly-OH | 0.15 | 0.23 | +29.0 |
| H-D-Lys-Tyr-D-Lys-Phe-Gly-OH | 0.15 | 0.23 | +3.5 |
| H-Har-Tyr-D-Arg-Phe-D-Ala-NH$_2$ | 0.51 | 0.84 | +40.7 |
| H-D-Har-Tyr-D-Arg-Phe-D-Ala-NH$_2$ | 0.51 | 0.84 | +17.1 |
| H-Cyt-Tyr-D-Arg-Phe-D-Ala-NH$_2$ | 0.48 | 0.62 | |
| H-D-Cyt-Tyr-D-Arg-Phe-D-Ala-NH$_2$ | 0.48 | 0.62 | |
| H-Tyr-D-Ala-Phe-Gly-OH | 0.56 | 0.70 | +10.1 |
| H-Tyr-D-Lys-Phe-Gly-OH | 0.59 | 0.71 | +30.3 |
| H-Tyr-D-Har-Phe-Gly-OH | 0.60 | 0.84 | +24.7 |
| H-Tyr-D-Orn-Phe-Gly-OH | 0.57 | 0.71 | +33.8 |
| H-Tyr-D-Arg-Phe-Gly-OH | 0.59 | 0.73 | +27.0 |
| H-Tyr-D-Orn-Phe-D-Glu-OH | 0.55 | 0.73 | +35.3 |
| H-Tyr-D-Arg-Phe-D-Glu-OH | 0.60 | 0.77 | +27.7 |
| H-Tyr-D-Orn-Phe-D-Ala-NH$_2$ | 0.63 | 0.80 | +10.6 |
| H-Tyr-D-Arg-Phe-D-Ala-NH$_2$ | 0.60 | 0.78 | +11.3 |
| H-Tyr-D-Val-Phe-D-Ala-NH$_2$ | 0.43 | 0.69 | |
| H-Tyr-D-Leu-Phe-D-Ala-NH$_2$ | 0.41 | 0.58 | |
| H-Tyr-D-Ile-Phe-D-Ala-NH$_2$ | 0.40 | 0.57 | |
| H-Tyr-D-Phe-Phe-D-Ala-NH$_2$ | 0.42 | 0.71 | |
| H-Tyr-D-Asn-Phe-D-Ala-NH$_2$ | 0.40 | 0.63 | |
| H-Tyr-D-Trp-Phe-D-Ala-NH$_2$ | 0.38 | 0.56 | |
| H-Tyr-D-Pro-Phe-D-Ala-NH$_2$ | 0.41 | 0.70 | |
| H-Tyr-D-Ser-Phe-D-Ala-NH$_2$ | 0.54 | 0.74 | |
| H-Tyr-D-Thr-Phe-D-Ala-NH$_2$ | 0.55 | 0.76 | |
| H-Tyr-D-Tyr-Phe-D-Ala-NH$_2$ | 0.48 | 0.61 | |
| H-Tyr-D-Hyp-Phe-D-Ala-NH$_2$ | 0.43 | 0.71 | |
| H-Tyr-D-Cys-Phe-D-Ala-NH$_2$ | 0.43 | 0.62 | |
| H-Tyr-D-Cys-Cys-Phe-D-Ala-OH | 0.40 | 0.65 | |
| H-Tyr-D-Met-Phe-D-Ala-NH$_2$ | 0.44 | 0.58 | |
| H-Tyr-D-His-Phe-D-Ala-NH$_2$ | 0.45 | 0.70 | |
| H-Tyr-D-Asp-Phe-D-Ala-NH$_2$ | 0.51 | 0.69 | |
| H-Tyr-D-Glu-Phe-D-Ala-NH$_2$ | 0.55 | 0.73 | |
| H-Tyr-D-β-Ala-Phe-D-Ala-NH$_2$ | 0.48 | 0.59 | |
| H-Arg-Tyr-D-Ala-Phe-Ala-OH | 0.53 | 0.70 | +38.4 |
| H-Arg-Tyr-D-Ala-Phe-Val-OH | 0.50 | 0.73 | +24.8 |
| H-Arg-Tyr-D-Ala-Phe-D-Val-OH | 0.50 | 0.73 | −0.4 |
| H-Arg-Tyr-D-Ala-Phe-Leu-OH | 0.51 | 0.72 | +36.3 |
| H-Arg-Tyr-D-Ala-Phe-D-Leu-OH | 0.51 | 0.72 | −0.8 |
| H-Arg-Tyr-D-Ala-Phe-Ile-OH | 0.51 | 0.73 | +33.6 |
| H-Arg-Tyr-D-Ala-Phe-D-Ile-OH | 0.51 | 0.73 | +4.3 |
| H-Arg-Tyr-D-Ala-Phe-Phe-OH | 0.52 | 0.69 | |
| H-Arg-Tyr-D-Ala-Phe-D-Phe-OH | 0.52 | 0.69 | |
| H-Arg-Tyr-D-Ala-Phe-Asn-OH | 0.48 | 0.68 | |
| H-Arg-Tyr-D-Ala-Phe-D-Asn-OH | 0.48 | 0.68 | |
| H-Arg-Tyr-D-Ala-Phe-Gln-OH | 0.50 | 0.70 | |
| H-Arg-Tyr-D-Ala-Phe-D-Gln-OH | 0.50 | 0.70 | |
| H-Arg-Tyr-D-Ala-Phe-Trp-OH | 0.51 | 0.71 | |
| H-Arg-Tyr-D-Ala-Phe-D-Trp-OH | 0.51 | 0.71 | |
| H-Arg-Tyr-D-Ala-Phe-Pro-OH | 0.53 | 0.72 | |
| H-Arg-Tyr-D-Ala-Phe-D-Pro-OH | 0.53 | 0.72 | |
| H-Arg-Tyr-D-Ala-Phe-Ser-OH | 0.52 | 0.71 | |
| H-Arg-Tyr-D-Ala-Phe-D-Ser-OH | 0.52 | 0.71 | |
| H-Arg-Tyr-D-Ala-Phe-Thr-OH | 0.51 | 0.68 | |
| H-Arg-Tyr-D-Ala-Phe-D-Thr-OH | 0.51 | 0.68 | |
| H-Arg-Tyr-D-Ala-Phe-Tyr-OH | 0.54 | 0.74 | |
| H-Arg-Tyr-D-Ala-Phe-D-Tyr-OH | 0.54 | 0.74 | |
| H-Arg-Tyr-D-Ala-Phe-Hyp-OH | 0.52 | 0.73 | |
| H-Arg-Tyr-D-Ala-Phe-D-Hyp-OH | 0.52 | 0.73 | |
| H-Arg-Tyr-D-Ala-Phe-Cys-OH | 0.50 | 0.63 | |
| H-Arg-Tyr-D-Ala-Phe-D-Cys-OH | 0.50 | 0.63 | |
| H-Arg-Tyr-D-Ala-Phe-Cys-Cys-OH | 0.48 | 0.65 | |
| H-Arg-Tyr-D-Ala-Phe-Cys-D-Cys-OH | 0.48 | 0.65 | |
| H-Arg-Tyr-D-Ala-Phe-D-Cys-Cys-OH | 0.48 | 0.65 | |
| H-Arg-Tyr-D-Ala-Phe-D-Cys-D-Cys-OH | 0.48 | 0.65 | |
| H-Arg-Tyr-D-Ala-Phe-Met-OH | 0.55 | 0.70 | +38.4 |
| H-Arg-Tyr-D-Ala-Phe-D-Met-OH | 0.55 | 0.70 | +8.3 |
| H-Arg-Tyr-D-Ala-Phe-Lys-OH | 0.58 | 0.74 | +18.3 |
| H-Arg-Tyr-D-Ala-Phe-D-Lys-OH | 0.58 | 0.74 | −12.1 |
| H-Arg-Tyr-D-Ala-Phe-Arg-OH | 0.16 | 0.65 | |
| H-Arg-Tyr-D-Ala-Phe-D-Arg-OH | 0.16 | 0.65 | |
| H-Arg-Tyr-D-Ala-Phe-His-OH | 0.18 | 0.58 | |
| H-Arg-Tyr-D-Ala-Phe-D-His-OH | 0.18 | 0.58 | |
| H-Arg-Tyr-D-Ala-Phe-Asp-OH | 0.48 | 0.63 | |
| H-Arg-Tyr-D-Ala-Phe-D-Asp-OH | 0.48 | 0.63 | |
| H-Arg-Tyr-D-Ala-Phe-Glu-OH | 0.51 | 0.74 | |
| H-Arg-Tyr-D-Ala-Phe-β-Ala-OH | 0.51 | 0.74 | |
| H-Arg-Tyr-D-Ala-Phe-D-β-Ala-OH | 0.16 | 0.58 | |
| H-Arg-Tyr-D-Ala-Phe-Orn-OH | 0.58 | 0.73 | |
| H-Arg-Tyr-D-Ala-Phe-D-Orn-OH | 0.58 | 0.73 | |

TABLE 2

| Peptide | IC$_{50}$ GPI | IC$_{50}$ MVD |
|---|---|---|
| H-Arg-Tyr-D-Ala-Phe-Gly-OH | 6.1 | <5 |
| H-Arg-Tyr-D-Lys-Phe-Gly-OH | 6.6 | 5.0 |
| H-Arg-Tyr-D-Orn-Phe-Gly-OH | 5.4 | <5 |
| H-Arg-Tyr-D-Ala-Phe-D-Ala-OH | 6.1 | 5.6 |
| H-Arg-Tyr-D-Orn-Phe-D-Ala-OH | 6.1 | <5 |
| H-Arg-Tyr-D-Arg-Phe-D-Ala-OH | 6.8 | 5.8 |
| H-Arg-Tyr-D-Arg-Phe-D-Ala-NH$_2$ | 6.7 | <5 |
| H-D-Arg-Tyr-D-Arg-Phe-D-Ala-NH$_2$ | 5.0 | <5 |
| H-Tyr-D-Har-Phe-Gly-OH | 6.5 | — |
| H-Tyr-D-Orn-Phe-Gly-OH | 6.4 | <5 |
| H-Tyr-D-Arg-Phe-Gly-OH | 7.5 | <5 |
| H-Tyr-D-Orn-Phe-D-Glu-OH | 4.7 | <5 |
| H-Tyr-D-Arg-Phe-D-Glu-OH | <5 | <5 |
| H-Tyr-D-Orn-Phe-D-Ala-NH$_2$ | 5.4 | <5 |
| H-Tyr-D-Ala-Phe-Gly-NH$_2$ | 1.6 | 0.03 |
| H-Tyr-D-Ala-Phe-Gly-OH | 2.8 | 2.0 |
| H-Tyr-D-Met-Phe-Gly-NH$_2$ | 0.1 | 0.2 |
| H-Tyr-D-Ala-Phe-β-Ala-OH | 0.6 | 0.9 |
| H-Tyr-D-Ala-Phe-β-Ala-NH$_2$ | 3.0 | 4.5 |

TABLE 3

| Group No | Peptide dose, μg/kg | Length increase, mm | Length increase, % (relative to control) |
|---|---|---|---|
| 1 | — | 4.2 | 0 |
| 2 | 1 | 4.4 | 4.5 |
| 3 | 10 | 4.9 | 16.7 |
| 4 | 100 | 4.5 | 17.9 |

TABLE 4

| Group No | Peptide Dose, μg/kg | Weight increase, % | Weight gain, % (relative to control) |
|---|---|---|---|
| 1 | — | 260 | 0 |
| 2 | 0.1 | 270 | 3.8 |
| 3 | 0.5 | 275 | 5.7 |
| 4 | 1.0 | 310 | 19.0 |

TABLE 5

| Group No | Peptide dose, μg/kg | Food consumption g/day/animal |
|---|---|---|
| 1 | — | 14.5 |
| 2 | 0.1 | 15.5 |
| 3 | 0.5 | 14.5 |
| 4 | 1.0 | 16.0 |

TABLE 6

| Group No | Peptide dose, μg/kg | Weight increase, % | Weight gain, % (relative to control) |
|---|---|---|---|
| 1 | — | 68 | 0 |
| 2 | 1.0* | 142 | 108 |
| 3 | 10.0* | 105 | 54 |
| 4 | 100.0* | 90 | 32 |
| 5 | 0.1** | 80 | 18 |
| 6 | 0.5** | 70 | 3 |
| 7 | 1.0** | 65 | −0.4 |

*oral administration
**intraperitoneal administration

TABLE 7

| Group No | Peptide dose, μg/kg | Food consumption g/day/animal |
|---|---|---|
| 1 | — | 5.6 |
| 2 | 1.0* | 7.0 |
| 3 | 10.0* | 5.0 |
| 4 | 100.0* | 5.5 |
| 5 | 0.1** | 5.3 |
| 6 | 0.5** | 5.2 |
| 7 | 1.0** | 5.8 |

*oral administration
**intraperitoneal administration

TABLE 8

| Group No | Peptide dose, μg/kg | Weight gain, % (relative to control) |
|---|---|---|
| 1 | — | 100 |
| 2 | 1.0* | 128.1 |
| 3 | 10.0* | 136.5 |
| 4 | 100.0* | 127 |
| 5 | 0.1** | 110.4 |
| 6 | 0.5** | 115.3 |
| 7 | 1.0** | 97 |

*oral administration
**intraperitoneal administration

TABLE 9

| Group No | Peptide dose, μg/kg | Weight increase, % | Weight gain, % |
|---|---|---|---|
| 1 | — | 10.2 | 100 |
| 2 | 8 | 10.4 | 102 |
| 3 | 12 | 12.5 | 122.6 |
| 4 | 16 | 11.8 | 115.7 |
| 5 | 20 | 11.6 | 113.7 |

*oral administration
**intraperitoneal administration

TABLE 10

| Group No | Peptide dose, μg/kg | Weight increase, kg female | Weight increase, kg male | Weight gain, % female | Weight gain, % male |
|---|---|---|---|---|---|
| Minks |||||| 
| 1 | — | 0.419 | 0.611 | 100 | 100 |
| 2 | 10 | 0.375 | 0.728 | 90 | 119 |
| 3 | 10 | 0.381 | 0.726 | 91 | 119 |
| 4 | 20 | 0.443 | 0.771 | 106 | 126 |
| Arctic foxes |||||| 
| 1 | — | 0.700 | 0.580 | 100 | 100 |
| 2 | 10 | 1.780 | 0.830 | 105 | 116 |
| 3 | 10 | 1.740 | 1.890 | 102 | 120 |
| 4 | 20 | 1.810 | 1.920 | 106 | 121 |

TABLE 11

| Group No | Peptide dose, μg/kg | Weight increase, % | Weight gain, % |
|---|---|---|---|
| 1 | — | 52 ± 3.9 | 100 |
| 2 | 1.0* | 60 ± 5.1 | 115 |
| 3 | 5.0* | 56 ± 4.8 | 108 |
| 4 | 10.0* | 68 ± 4.9 | 130 |
| 5 | 0.1** | 57 ± 3.7 | 109 |
| 6 | 0.5** | 59 ± 4.1 | 114 |
| 7 | 1.0** | 62 ± 1.2 | 118 |

*- oral administration
**- intraperitoneal administration

TABLE 12

| Group No | Peptide dose, μg/kg | Weight increase, % | Weight gain, % |
|---|---|---|---|
| 1 | — | 24.6 | 100 |
| 2 | 1.0* | 27.2 | 110 |
| 3 | 5.0* | 26.1 | 106 |
| 4 | 10.0* | 34.6 | 142 |
| 5 | 0.1** | 30.3 | 123 |
| 6 | 0.5** | 29.7 | 121 |
| 7 | 1.0** | 37.6 | 153 |

*- oral administration
**- intramuscular administration

TABLE 13

| Description | Control | Test |
|---|---|---|
| Number of Bulls | 12 | 12 |
| Animal's weight at start of experiment (kg) | 72.2 ± 1.1 | 72.3 ± 0.9 |
| Animal's weight at end of experiment (kg) | 261.2 ± 4.1 | 305.5 ± 5.3 |

TABLE 13-continued

| Description | Control | Test |
|---|---|---|
| Weight increase during test period (kg) | 189.0 ± 2.7 | 233.2 ± 2.4 |
| Average daily weight increase (g) | 610 ± 15.8 | 752 ± 17.3 |

TABLE 14

| | Groups | |
|---|---|---|
| Description | control | test |
| The number of carps | 10 | 10 |
| Average weight (at the beginning). g | 31.6 ± 3.9 | 33.0 ± 4.9 |
| Average weight (at the end). g | 33.0 ± 4.7 | 40.6 ± 5.6 |
| "" to control | 100 | 123.0 |

TABLE 15

Body weight changes in white rats after 18-hour immobilization.

| Dose, (μg/kg) | Weight before immobiliz- ation, g | Weight after immobiliz- ation, g | % weight loss | % relative to control |
|---|---|---|---|---|
| Control | 174, 75 | 160, 75 | 8, 38 | 100, 0 |
| 10, 0 | 174, 35 | 160, 90 | 6, 85 | 83, 15 |
| 100, 0 | 180, 30 | 167, 90 | 6, 84 | 82, 80 |

TABLE 16

Evaluation of stomach ulceration in white rats after 18-hour immobilization

| Dose, (μg/kg) | Animals, n | Animals with ulceration, % | Total length of ulceration | % relative to control |
|---|---|---|---|---|
| Control | 15 | 80, 0 | 3, 22 ± 1, 59 | 100, 0 |
| 10, 0 | 20 | 25, 0 | 0, 75 ± 0, 52 | 23, 3 |
| 100, 0 | 20 | 0, 0 | 0, 0 | 0, 0 |

TABLE 17

Weight coefficients of the internals in white rats after 18-hour immobilization (μg per 100 g body weight)

| Preparation, dose, μg/kg | Adrenal glands | Spleen | Thymus |
|---|---|---|---|
| Intact | 0, 17 ± 0, 01 | 4, 95 ± 0, 70 | 4, 22 ± 0, 26 |
| Control | 0, 25 ± 0, 02 | 3, 33 ± 0, 20 | 4, 07 ± 0, 19 |
| 10, 0 | 0, 22 ± 0, 01 | 2, 50 ± 0, 19 | 3, 77 ± 0, 16 |
| 100, 0 | 0, 17 ± 0, 02 | 2, 74 ± 0, 29 | 4, 47 ± 0, 14 |

TABLE 18

Combined data of evaluation of the preparation adaptogenic activity under mental-and-exercise stress

| Dose, (μg/kg) | Swimming duration, s | Protection rate (PR) | PR by the 1st hour | PR by the 3rd hour |
|---|---|---|---|---|
| Control | 287, 60 ± 37, 29 | 1,000 | — | — |
| 1, 0 | 361, 90 ± 38, 36 | 1,258 | — | — |
| 10, 0 | 318, 45 ± 21, 71 | 1,107 | — | — |
| 100, 0 | 431, 10 ± 43, 16 | 1,500 | — | — |
| 1000, 0 | 373, 75 ± 39, 86 | 1,334 | — | — |
| Three hours after the first swimming | | | | |
| Control | 284,90 ± 30, 79 | 1,000 | 0,991 | — |
| 1, 0 | 385,85 ± 36, 88 | 1,354 | 1,066 | — |
| 10, 0 | 359,30 ± 29, 34 | 1,261 | 1,128 | — |
| 100, 0 | 424,35 ± 43, 21 | 1,489 | 0,984 | — |
| 1000, 0 | 382,70 ± 49, 85 | 1,343 | 1,024 | — |
| 24 hours after the first swimming | | | | |
| Control | 303, 75 ± 27, 82 | 1,000 | 1,056 | 1,066 |
| 1, 0 | 530, 45 ± 60, 81 | 1,746 | 1,466 | 1,374 |
| 10, 0 | 626, 20 ± 48, 59 | 2,062 | 1,966 | 1,623 |
| 100, 0 | 424, 40 ± 61, 83 | 1,397 | 0,984 | 1,000 |
| 1000, 0 | 404, 96 ± 58, 20 | 1,333 | 1,084 | 1,058 |

TABLE 19

Evaluation of the preparation adaptogenic activity under mental-and-exercise stress

| Test conditions | Control | 10.0 (μg/kg) | 100.0 (μg/kg) |
|---|---|---|---|
| Swimming (hypothermia +15° C.), males | | | |
| 1 hour after injection | 183, 3 ± 13, 68 | 234, 3 ± 19, 63 | 238, 6 ± 22, 42 |
| 3 hours after 1st swimming | 196, 6 ± 21, 03 | 209, 9 ± 22, 98 | 237, 7 ± 14, 93 |
| Swimming (hyperthermia +40° C.), males | | | |
| 1 hour after injection | 545, 0 ± 58, 38 | 394, 2 ± 42, 86 | 640, 7 ± 100, 32 |
| 3 hours after 1st swimming | 352, 3 ± 82, 69 | 202, 3 ± 44, 41 | 277, 0 ± 68, 46 |
| After 24 hours | 498, 3 ± 36, 01 | 503, 2 ± 91, 4 | 682, 0 ± 53, 93 |

TABLE 20

Mean asleep time of mice after Medinal injection in the dose of 570 mg per kg body weight after preparation administration

| Preparation doses, (μg/kg) | | | |
|---|---|---|---|
| Asleep time, min | | | |
| 1.0 | 10.0 | 100.0 | Control |
| 19, 38 ± 1, 75 | 22, 38 ± 0, 81 | 20, 67 ± 1, 68 | 18, 19 ± 0, 66 |

TABLE 21

Survival rate, %, of mice after injection of the maximal Medinal dose (570 mg per kg body weight) after preparation administration

| Survival rate, % | Preparation doses, (μg/kg) | | | |
|---|---|---|---|---|
| | 1.0 | 10.0 | 100.0 | Control |
| 48 hours following injection | 55, 6 | 88, 9 | 88, 9 | 44, 4 |

TABLE 21-continued

Survival rate, %, of mice after injection of the maximal Medinal dose (570 mg per kg body weight) after preparation administration

| Survival rate, % | Preparation doses, (μg/kg) | | | |
|---|---|---|---|---|
| | 1.0 | 10.0 | 100.0 | Control |
| 24 hours following injection | 22, 2 | 77, 8 | 44, 4 | 33, 3 |

We claim:

1. A method for preventing or reducing conditions or complications resulting from stress in an animal in need thereof, comprising administering to said animal an effective amount of a peptide of the formula I, X-Tyr-Y-Phe-Z-A   I wherein X is hydrogen, arginine, D-arginine, ornithine, D-ornithine, lysine, D-lysine, homoarginine, D-homoarginine, citrulline, D-citrulline; Tyr is tyrosine; Y is D-alanine, D-valine, D-leucine, D-isoleucine, D-phenylalanine, D-asparagine, D-tryptophan, D-proline, D-serine, D-threonine, D-tyrosine, D-hydroxyproline, D-cysteine, D-cysteyl-cysteine, D-methionine, D-lysine, D-homoarginine, D-arginine, D-histidine, D-aspartic acid, D-glutamic acid, D-β-alanine, or D-ornithine Phe is phenylalanine; Z is alanine, D-alanine, valine, D-valine, leucine, D-leucine, isoleucine, D-isoleucine, phenylalanine, D-phenylalanine, asparagine, D-asparagine, glycine, glutamine, D-glutamine, tryptophan, D-tryptophan, proline, D-proline, serine, D-serine, threonine, D-threonine, tyrosine, D-tyrosine, hydroxyproline, D-hydroxyproline, cysteine, D-cysteine, cysteyl-cysteine, cysteine-D-cysteine, D-cysteyl-cysteine, D-cysteine-D-cysteine, methionine, D-methionine, lysine, D-lysine, arginine, D-arginine, histidine, D-histidine, aspartic acid, D-aspartic acid, glutamic acid, D-glutamic acid, β-alanine, D-β-alanine, ornithine, or D-ornithine; and A is hydroxyl or an amide which may be substituted, wherein when X is H and Y is D-Arg Z-A is not Lys-$NH_2$; and when X is H, and Y is Pro, Z-A is not Pro-OH or Pro-$NH_2$.

2. A method according to claim 1, wherein X is Arg, D-Arg, D-Orn, homoarginine, D-homoarginine, or citrulline; Y is D-Orn, D-Ala, or D-Arg; Z is D-Ala, Gly, Pro, D-Pro or β-Ala; and A is OH or $NH_2$.

3. method according to claim 2 wherein when X is Arg and Y is D-Ala, then Z is not Pro; and when X is D-Arg and Y is D-Ara then Z is not D-Ala.

4. A method according to claim 3 wherein when X is Arg, Y is D-Ala, Z is D-Pro or β-Ala; and A is OH.

5. A method according to claim 2 wherein when X is D-Arg and Y is D-Arg, then Z is not D-Ala.

6. A method according to claim 1, wherein X is Arg, homoarginine, D-homoarginine, citrulline, or D-citrulline; Y is D-Ala, D-Orn, or D-Arg; Z is D-Ala; and A is OH or $NH_2$.

7. A method according to claim 1, wherein X is Arg; Y is D-Ala; Z is D-Pro, Pro, or β-Ala; and, A is OH.

8. A method according to claim 1, wherein X is H-D-Arg-Tyr-D-Arg-Phe-D-Ala-$NH_2$, H-D-Orn-Tyr-D-Ala-Phe-D-Ala-OH, H-Arg-Tyr-D-Ala-Phe-β-Ala-OH, H-Arg-Tyr-D-Ala-Phe-Gly-OH; H-Har-Tyr-D-Arg-Phe-D-Ala-$NH_2$; H-D-Har-Tyr-D-Arg-Phe-D-Ala-$NH_2$; H-Cyt-Tyr-D-Arg-Phe-D-Ala-$NH_2$; H-D-Cyt-Tyr-D-Arg-Phe-D-Ala-$NH_2$; H-Arg-Tyr-D-Ala-Phe-Pro-OH; H-Arg-Tyr-D-Ala-Phe-D-Pro-OH; H-Arg-Tyr-D-Ala-Phe-D-Ala-OH; H-Arg-Tyr-D-Orn-Phe-D-Ala-OH; H-Arg-Tyr-D-Arg-Phe-D-Ala-OH; H-Arg-Tyr-D-Arg-Phe-D-Ala-$NH_2$; or H-Tyr-D-Orn-Phe-D-Glu-OH.

9. A method according to claim 8 wherein the peptide is Arg-Tyr-D-Ala-Phe-Glyn-OH.

10. A method according to claim 1 wherein the stress is physical stress.

11. A method according to claim 10 wherein the physical stress is physical exercise.

12. A method according to claim 1 wherein the stress is mental stress.

13. A method according to claim 1 wherein the conditions or complications resulting from stress is an ulcer.

* * * * *

UNITED STATES PATENT AND TRADEMARK OFFICE
CERTIFICATE OF CORRECTION

PATENT NO. : 6,248,716 B1
DATED : June 19, 2001
INVENTOR(S) : Vladislav I. Deigin and Yelena Yarova It is certified that error appears in the above-identified patent and that said Letters Patent is hereby corrected as shown below:

Title page,
The title incorrectly reads:
"PEPTIDE, A METHOD FOR ITS PREPARATION AND A PHARMACEUTICAL COMPOSITION CONTAINING THE PEPTIDE" and is hereby changed to read
-- NOVEL PEPTIDE, A METHOD FOR ITS PREPARATION AND A PHARMACEUTICAL COMPOSITION CONTAINING THE PEPTIDE --

Column 4,
Line 16, the description incorrectly reads as follows: "is Arg and Y is D-Ala, the Z is not Pro" and is hereby changed to read -- is Arg and Y is D-Ala, then Z is not Pro --

Column 27, claim 1,
Line 29, incorrectly reads "D-glutamic acid, D-ß-alanine, or D-ornithine Phe is pheny-" and is hereby changed to read -- D-glutamic acid, D-ß-alanine, or D-ornithine; Phe is pheny- --

Column 28, claim 1,
Line 1, incorrectly reads "D-Arg Z-A is not Lys-NH$_2$; and when X is H, and Y is Pro," and is hereby changed to read -- D-Arg, Z-A is not Lys-NH$_2$; and when X is H, and Y is Pro, --

Column 28, claim 3,
Lines 7-9, incorrectly reads "method according to claim 2 wherein when X is Arg and Y is D-Ala, then Z is not Pro; and when X is D-Arg and Y is D-Ara then Z is not D-Ala." and is hereby changed to read -- A method according to claim 2 wherein when X is Arg and Y is D-Ala, then Z is not Pro; and when X is D-Arg and Y is D-Arg then Z is not D-Ala. --

UNITED STATES PATENT AND TRADEMARK OFFICE
CERTIFICATE OF CORRECTION

PATENT NO. : 6,248,716 B1
DATED : June 19, 2001
INVENTOR(S) : Vladislav I. Deigin and Yelena Yarova It is certified that error appears in the above-identified patent and that said Letters Patent is hereby corrected as shown below:

Column 28, claim 9,
Lines 31-32, incorrectly reads,
"A method according to claim 8 wherein the peptide is Arg-Tyr-D-Ala-Phe-Glyn-OH." and is hereby changed to read -- A method according to claim 8 wherein the peptide is Arg-Tyr-D-Ala-Phe-Gly-OH. --

Signed and Sealed this

Twentieth Day of November, 2001

Attest:

*Attesting Officer*

NICHOLAS P. GODICI
*Acting Director of the United States Patent and Trademark Office*